US007745454B2

(12) United States Patent
Konradi et al.

(10) Patent No.: US 7,745,454 B2
(45) Date of Patent: *Jun. 29, 2010

(54) ALPHA AMINO ACID DERIVATIVES-INHIBITORS OF LEUKOCYTE ADHESION MEDIATED BY VLA-4

(75) Inventors: Andrei W. Konradi, San Francisco, CA (US); Michael A. Pleiss, Sunnyvale, CA (US); Eugene D. Thorsett, Half Moon Bay, CA (US); Susan Ashwell, Plainsboro, NJ (US); Gregory S. Welmaker, Jackson, NJ (US); Anthony Kreft, Langhorne, PA (US); Dimitrios Sarantakis, Newton, PA (US); Darren B. Dressen, San Francisco, CA (US); Francine S. Farouz, Mercer Island, WA (US); Christopher M. Semko, Fremont, CA (US); Ying-Zi Xu, Palo Alto, CA (US)

(73) Assignees: Elan Pharmaceuticals, Inc., South San Francisco, CA (US); Wyeth, Madison, NJ (US)

( * ) Notice: Subject to any disclaimer, the term of this patent is extended or adjusted under 35 U.S.C. 154(b) by 619 days.

This patent is subject to a terminal disclaimer.

(21) Appl. No.: 10/936,070

(22) Filed: Sep. 7, 2004

(65) Prior Publication Data
US 2005/0085459 A1    Apr. 21, 2005

Related U.S. Application Data

(63) Continuation of application No. 09/910,702, filed on Jul. 20, 2001, now Pat. No. 6,803,370.

(60) Provisional application No. 60/220,132, filed on Jul. 21, 2000.

(51) Int. Cl.
A61K 31/505      (2006.01)
A61K 31/515      (2006.01)
C07D 239/22      (2006.01)
C07D 239/42      (2006.01)
A61P 19/02       (2006.01)
A61P 11/06       (2006.01)
A61P 37/08       (2006.01)

(52) U.S. Cl. .................. 514/269; 514/272; 544/297; 544/319

(58) Field of Classification Search ............ 514/252.01, 514/252.02, 252.03, 269, 272; 544/238, 544/297, 319
See application file for complete search history.

(56) References Cited

U.S. PATENT DOCUMENTS

| | | | | |
|---|---|---|---|---|
| 5,510,332 | A | 4/1996 | Kogan et al. | 514/14 |
| 6,348,463 | B1 * | 2/2002 | Head et al. | 514/241 |
| 6,683,079 | B2 | 1/2004 | Bisagni et al. | 514/233.5 |
| 6,803,370 | B2 * | 10/2004 | Konradi et al. | 514/400 |

FOREIGN PATENT DOCUMENTS

| | | |
|---|---|---|
| EP | 330506 | 8/1989 |
| WO | 96/01644 | 1/1996 |
| WO | 99-37618 | 7/1999 |
| WO | 00/43369 | 7/2000 |

OTHER PUBLICATIONS

Doherty, G.A. et. al., Bioorg. & Med. Chem. Lett., vol. 12, 2002, pp. 729-731.*
von Andrian et. al., "alpha4 Integrins as Therapeutic Targets . . . " New England J Med, 2003, vol. 348, pp. 68-72.*
Miller et. al., "A Controlled Trial for Natalizumab . . . ", New England J Med, 2003, vol. 348, pp. 15-23.*
Ghosh et. al., "Natalizumab for Active Crohn's Disease" New England J Med, 2003, vol. 348, pp. 24-32.*
Yusuf-Makagiasar et. al., "Inhibition of LFA-1/ICAM-1 and VLA-4/VCAM-1 . . . " Med. Res. Rev., 2002, vol. 22, No. 2, pp. 146-167.*
Yang et. al., "VLA-4 Antagonists: . . . " Med. Res. Rev., 2003, vol. 23, No. 3, pp. 369-392.*
Vanderslice et. al., "Development of cell adhesion molecules antagonists . . . " Pulmon. Pharm. & Thera., 2001, vol. 17, pp. 1-10.*
Tilley, J. W., "VLA-4 antagonists", Expert Opin. Ther. Patents (2002), vol. 12, No. 7, pp. 991-1008.*
Kuzemko, I., et al., "Synthesis and Properties of N-(2-Chloro-6-ethyl-4-Pyrimidinyl) Amino Acids", *Fiziol. Aktriv. Veshchestva*, vol. 5, pp. 101-105 (1973) (Russian) English abstract submitted.
Yednock, et al. *Nature*, vol. 356, pp. 63-66, (1992).
Abraham, et al., *J. Clin. Invest.*, vol. 93, pp. 776-787, (1994).
Bao, et al., *Diff*, vol. 52, pp. 239-246 (1993).
Baron, et al., *J. Clin. Invest.*, vol. 93, pp. 1700-1708 (1994).
Baron, et al., *J. Exp. Med.*, vol. 177, pp. 57-68 (1993).
Burkly, et al., *Diabetes*, vol. 43, pp. 529-534 (1994).
Cybulsky, et al., Science vol. 251, pp. 788-791 (1991).
Elices, et al., *Cell*, vol. 60, pp. 577-584 (1990).
Elices, et al., *J. Clin. Invest.*, vol. 93, 99. 405-416 (1994).
Hamann, et al., *J. Immunology*, vol. 152, pp. 3282-3293 (1994).
Kawaguchi, et al., *Japanese J. Cancer Res.*, vol. 83, pp. 1304-1316 (1992).
Lauri, et al., *British J. Cancer*, vol. 68, pp. 862-867 (1993).
Li, et al., *Arterioscler. Thromb.*, vol. 13 (2), pp. 197-204 (1993).
Mulligan, et al. *J. Immunology*, vol. 150 (6), pp. 2407-2417, 1993.

(Continued)

Primary Examiner—James O Wilson
Assistant Examiner—Tamthom N Truong
(74) Attorney, Agent, or Firm—Swiss Tanner, P.C.

(57) ABSTRACT

Disclosed are certain alpha amino acid compounds which bind VLA-4. Certain of these compounds also inhibit leukocyte adhesion and, in particular, leukocyte adhesion mediated by VLA-4. Such compounds are useful in the treatment of inflammatory diseases in a mammalian patient, e.g., human, such as asthma, Alzheimer's disease, atherosclerosis, AIDS dementia, diabetes, inflammatory bowel disease, rheumatoid arthritis, tissue transplantation, tumor metastasis and myocardial ischemia. The compounds can also be administered for the treatment of inflammatory brain diseases such as multiple sclerosis.

12 Claims, No Drawings

OTHER PUBLICATIONS

Okarhara, et al., *Can. Res.*, vol. 54, pp. 3233-3236 (1994).
Paavonen, et al., *Int. J. Can.*, vol. 58, pp. 298-302 (1994).
Paul, et al., *Transpl. Proceed.*, vol. 25 (1), pp. 813-814 (1993).
Postigo, et al., *J. Clin. Invest.*, vol. 89, pp. 1445-1452 (1991).
Pretolani, et al., *J. Exp. Med.*, vol. 180, pp. 795-805 (1994).
Sasseville, et al., *Am. J. Path.*, vol. 144, pp. 27-40 (1994).
Osborn, *Cell*, vol. 62, pp. 3-6 (1990).

* cited by examiner

ALPHA AMINO ACID DERIVATIVES-INHIBITORS OF LEUKOCYTE ADHESION MEDIATED BY VLA-4

CROSS REFERENCE TO RELATED APPLICATIONS

This application is a continuation of U.S. patent application Ser. No. 09/910,702, filed Jul. 21, 2001 which application claims the benefit of U.S. patent application Ser. No. 60/220,132, filed Jul. 21, 2000, the disclosures of which are incorporated herein by reference in their entirety.

BACKGROUND OF THE INVENTION

Field of the Invention

This invention relates to certain alpha amino acid derivatives which inhibit leukocyte adhesion and, in particular, leukocyte adhesion mediated by VLA-4.

REFERENCES

The following publications, patents and patent applications are cited in this application as superscript numbers:
[1] Hemler and Takada, European Patent Application Publication No. 330,506, published Aug. 30, 1989
[2] Elices, et al., *Cell*, 60:577-584 (1990)
[3] Springer, *Nature*, 346:425-434 (1990)
[4] Osborn, *Cell*, 62:3-6 (1990)
[5] Vedder, et al., *Surgery*, 106:509 (1989)
[6] Pretolani, et al., *J. Exp. Med.*, 180:795 (1994)
[7] Abraham, et al. *J. Clin. Invest.*, 93:776 (1994)
[8] Mulligan, et al., *J. Immunology*, 150:2407 (1993)
[9] Cybulsky, et al., *Science*, 251:788 (1991)
[10] Li, et al., *Arterioscler. Thromb.*, 13:197 (1993)
[11] Sasseville, et al., *Am. J. Path.*, 144:27 (1994)
[12] Yang, et al., *Proc. Nat. Acad. Science (USA)*, 90:10494 (1993)
[13] Burkly, et al., *Diabetes*, 43:529 (1994)
[14] Baron, et al., *J. Clin. Invest.*, 93:1700 (1994)
[15] Hamann, et al., *J. Immunology*, 152:3238 (1994)
[16] Yednock, et al., *Nature*, 356:63 (1992)
[17] Baron, et al., *J. Exp. Med.*, 177:57 (1993)
[18] van Dinther-Janssen, et al., *J. Immunology*, 147:4207 (1991)
[19] van Dinther-Janssen, et al., *Annals. Rheumatic Dis.*, 52:672 (1993)
[20] Elices, et al., *J. Clin. Invest.*, 93:405 (1994)
[21] Postigo, et al., *J. Clin. Invest.*, 89:1445 (1991)
[22] Paul, et al., *Transpl. Proceed.*, 25:813 (1993)
[23] Okarhara, et al., *Can. Res.*, 54:3233 (1994)
[24] Paavonen, et al., *Int. J. Clin.*, 58:298 (1994)
[25] Schadendorf, et al., *J. Pain.*, 170:429 (1993)
[26] Bao, et al., *Diff.*, 52:239 (1993)
[27] Lauri, et al., *British J. Cancer*, 68:862 (1993)
[28] Kawaguchi, et al., *Japanese J. Cancer Res.*, 83:1304 (1992)
[29] Kogan, et al., U.S. Pat. No. 5,510,332, issued Apr. 23, 1996
[30] International Patent Appl. Publication No. WO 96/01644

All of the above publications, patents and patent applications are herein incorporated by reference in their entirety to the same extent as if each individual publication, patent or patent application was specifically and individually indicated to be incorporated by reference in its entirety.

STATE OF THE ART

VLA-4 (also referred to as $\alpha_4\beta_1$ integrin and CD49d/CD29), first identified by Hemler and Takada[1] is a member of the β1 integrin family of cell surface receptors, each of which comprises two subunits, an α chain and a β chain. VLA-4 contains an α4 chain and a β1 chain. There are at least nine β1 integrins, all sharing the same β1 chain and each having a distinct α chain. These nine receptors all bind a different complement of the various cell matrix molecules, such as fibronectin, laminin, and collagen. VLA-4, for example, binds to fibronectin. VLA-4 also binds non-matrix molecules that are expressed by endothelial and other cells. These non-matrix molecules include VCAM-1, which is expressed on cytokine-activated human umbilical vein endothelial cells in culture. Distinct epitopes of VLA-4 are responsible for the fibronectin and VCAM-1 binding activities and each activity has been shown to be inhibited independently.[2]

Intercellular adhesion mediated by VLA-4 and other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[3] and Osborn[4].

Inflammatory brain disorders, such as experimental autoimmune encephalomyelitis (EAE), multiple sclerosis (MS) and meningitis, are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive tissue damage resulting in impaired nerve conduction and paralysis.

In other organ systems, tissue damage also occurs via an adhesion mechanism resulting in migration or activation of leukocytes. For example, it has been shown that the initial insult following myocardial ischemia to heart tissue can be further complicated by leukocyte entry to the injured tissue causing still further insult (Vedder et al.[5]). Other inflammatory or medical conditions mediated by an adhesion mechanism include, by way of example, asthma[6-8], Alzheimer's disease, atherosclerosis[9-10], AIDS dementia[11], diabetes[12-14] (including acute juvenile onset diabetes), inflammatory bowel disease[15] (including ulcerative colitis and Crohn's disease), multiple sclerosis[16-17], rheumatoid arthritis[18-21], tissue transplantation[22] tumor metastasis[23-28], meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

In view of the above, assays for determining the VLA-4 level in a biological sample containing VLA-4 would be useful, for example, to diagnosis VLA-4 mediated conditions. Additionally, despite these advances in the understanding of leukocyte adhesion, the art has only recently addressed the use of inhibitors of adhesion in the treatment of inflammatory brain diseases and other inflammatory conditions[19,30]. The present invention addresses these and other needs.

SUMMARY OF THE INVENTION

This invention provides compounds which bind to VLA-4. Such compounds can be used, for example, to assay for the presence of VLA-4 in a sample and in pharmaceutical compositions to inhibit cellular adhesion mediated by VLA-4, for example, binding of VCAM-1 to VLA-4. The compounds of this invention have a binding affinity to VLA-4 as expressed by an $IC_{50}$ of about 15 μM or less (as measured using the procedures described in Example A below).

Accordingly, in one of its composition aspects, this invention is directed to a compound of Formula (Ia) or (Ib):

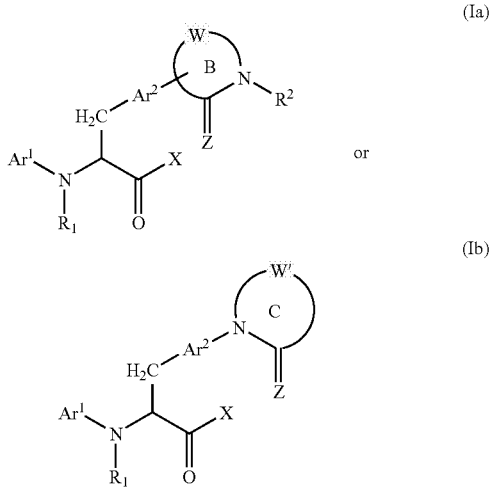

wherein:

Ar¹ is an aryl, heteroaryl, cycloalkyl, or heterocyclic group wherein said aryl, heteroaryl, cycloalkyl, or heterocyclic group is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where each R is independently hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, —N[S(O)₂—R']₂ and —N[S(O)₂—NR']₂ where each R' is independently selected from the group consisting of alkyl, substituted alkyl, aryl, substituted aryl, heteroaryl, substituted heteroaryl, heterocyclic and substituted heterocyclic;

R¹ is selected from the group consisting of hydrogen, alkyl, substituted alkyl, alkenyl, substituted alkenyl, cycloalkyl, substituted cycloalkyl, cycloalkenyl, substituted cycloalkenyl, aryl, substituted aryl, heteroaryl, substituted heteroaryl, heterocyclic and substituted heterocyclic;

Ar² is an aryl or heteroaryl group optionally substituted, in addition to ring B or C, with one or two substituent(s) selected from the group consisting of hydrogen, halogen, hydroxy, alkoxy, substituted alkoxy, acyloxy, amino, alkylamino, substituted alkylamino, dialkylamino, substituted dialkylamino, acylamino, aminoacyl, N-acyl-N-alkylamino, substituted N-acyl-N-alkylamino, (alkylsulfonyl)amino, substituted (alkylsulfonyl)amino, N-(alkylsulfonyl)-N-alkylamino, substituted N-(alkylsulfonyl)-N-alkylamino, alkyl, substituted alkyl, cycloalkyl, substituted cycloalkyl, alkenyl, substituted alkenyl, cycloalkenyl, substituted cycloalkenyl, alkynyl, substituted alkynyl, cyano, acyl, substituted acyl, carboxy, substituted carboxy, thiol, alkylthio, substituted alkylthio, alkylsulfoxy, substituted alkylsulfoxy, alkylsulfonyl, and substituted alkylsulfonyl;

Z is —O— or —S—;

B is a group wherein W, together with —C(=Z)NR²—, forms a saturated or unsaturated heterocyclic group containing 2 to 5 carbon atoms and 0 to 4 additional heteroatoms selected from the group consisting of nitrogen, oxygen, and —SO$_n$— (where n is 0 to 2) wherein said saturated or unsaturated heterocyclic group is optionally fused with one or two ring(s) structures selected from the group consisting of cycloalkyl, cycloalkenyl, heterocyclic, aryl and heteroaryl group to form a bi- or tri-fused ring system and further wherein said heterocyclic group and each of such ring structures are optionally substituted with 1 to 3 substituents selected from the group consisting of with one or two substituent(s) selected from the group consisting of hydrogen, halogen, hydroxy, alkoxy, substituted alkoxy, acyloxy, substituted acyloxy, amino, alkylamino, substituted alkylamino, dialkylamino, substituted dialkylamino, acylamino, substituted acylamino, N-acyl-N-alkylamino, substituted N-acyl-N-alkylamino, alkylene dioxy, (alkylsulfonyl)amino, substituted (alkylsulfonyl)amino, N-(alkylsulfonyl)-N-alkylamino, substituted N-(alkylsulfonyl)-N-alkylamino, alkyl, substituted alkyl, cycloalkyl, substituted cycloalkyl, alkenyl, substituted alkenyl, cycloalkenyl, substituted cycloalkenyl, alkynyl, substituted alkynyl, cyano, acyl, substituted acyl, carboxy, substituted carboxy, nitro, thiol, alkylthio, substituted alkylthio, alkylsulfoxy, substituted alkylsulfoxy, alkylsulfonyl, substituted alkylsulfonyl, aryl, substituted aryl, heteroaryl, substituted heteroaryl;

R² is selected from the group consisting of alkyl, substituted alkyl, aryl, substituted aryl, heteroaryl, substituted heteroaryl, cycloalkyl, substituted cycloalkyl, cycloalkenyl, and substituted cycloalkenyl;

C is a group wherein W', together with —C(=Z)N—, forms a saturated or unsaturated heterocyclic group containing 2 to 5 carbon atoms and 0 to 4 additional heteroatoms selected from the group consisting of nitrogen, oxygen, and —SO$_n$— (where n is 0 to 2) wherein said saturated or unsaturated heterocyclic group is optionally fused with one or two ring(s) structures selected from the group consisting of cycloalkyl, cycloalkenyl, heterocyclic, aryl and heteroaryl group to form a bi- or tri-fused ring system and further wherein said heterocyclic group and each of such ring structures are optionally substituted with 1 to 3 substituents selected from the group consisting of with one or two substituent(s) selected from the group consisting of hydrogen, halogen, hydroxy, alkoxy, substituted alkoxy, alkylenedioxy, acyloxy, substituted acyloxy, amino, alkylamino, substituted alkylamino, dialkylamino, substituted dialkylamino, acylamino, substituted acylamino, N-acyl-N-alkylamino, substituted N-acyl-N-alkylamino, (alkylsulfonyl)amino, substituted (alkylsulfonyl)amino, N-(alkylsulfonyl)-N-alkylamino, substituted N-(alkylsulfonyl)-N-alkylamino, alkyl, substituted alkyl, cycloalkyl, substituted cycloalkyl, alkenyl, substituted alkenyl, cycloalkenyl, substituted cycloalkenyl, alkynyl, substituted alkynyl, cyano, nitro, acyl, substituted acyl, carboxy, substituted carboxy, thiol, alkylthio, substituted alkylthio, alkylsulfoxy, substituted alkylsulfoxy, alkylsulfonyl, substituted alkylsulfonyl, aryl, substituted aryl, heteroaryl, substituted heteroaryl;

X is selected from the group consisting of hydroxyl, alkoxy, substituted alkoxy, alkenoxy, substituted alkenoxy, cycloalkoxy, substituted cycloalkoxy, cycloalkenoxy, substituted cycloalkenoxy, aryloxy, substituted aryloxy, heteroaryloxy, substituted heteroaryloxy, heterocyclyloxy, substituted heterocyclyloxy and —NR"R" where each R" is independently selected from the group consisting of hydrogen, alkyl, substituted alkyl, alkenyl, substituted alkenyl, cycloalkyl, substituted cycloalkyl, aryl, substituted aryl, heteroaryl, substituted heteroaryl, heterocyclic and substituted heterocyclic;

and enantiomers, diastereomers and pharmaceutically acceptable salts thereof;

and further wherein the compound of Formula I has a binding affinity to VLA-4 as expressed by an $IC_{50}$ of about 15 μM or less.

In a preferred embodiment, in compound (Ia), B is either:

(a) a group wherein W, together with —C(═Z)NR²— where Z is —O—, forms an unsaturated heterocyclic group containing 3 or 4 carbon atoms and 0 or 1 additional nitrogen atoms and further wherein the unsaturated heterocyclic group is optionally substituted, in addition to the R² group, with 1 or 2 substituents selected from the group consisting of alkyl, alkoxy, substituted alkoxy, alkenyloxy, substituted alkenyloxy, halo, hydroxy, mono or dialkylamino. Preferably B is 2-pyridone, (e.g., 2-pyridon-3-yl, 2-pyridon-4-yl, etc.,) or 6-pyrimidone (e.g., 6-pyrimidon-5-yl, etc.,) that is optionally substituted, in addition to the R² group, with 1 or 2 substituents selected from the group consisting of alkyl, alkoxy, substituted alkoxy, alkenyloxy, substituted alkenyloxy, halo, hydroxy, mono or dialkylamino, more preferably methyl, ethyl, propyl, methoxy, ethoxy, propoxy, butoxy, allyloxy, butenyloxy (wherein the methyl, ethyl, propyl, butyl, and allyl group in said methoxy, ethoxy, propoxy, butoxy, allyloxy, butenyloxy may be optionally substituted with one, two or three substituents selected from the group consisting of hydroxy, alkoxy, thiol, alkylthio, alkylsulfoxide, alkylsulfone, halo, alkylamino, dialkylamino, amino, aminoacyl, preferably, hydroxy, methoxy, ethoxy, methylthio, methylsulfane, methylsulfone, fluoro, methylamino, dimethylamino, amino, and acetylamino), chloro, bromo, hydroxy, methylamino, or dimethylamino. More preferably in the above rings R² is alkyl, preferably methyl; or (b) a group wherein W, together with —C(═Z)NR²— where Z is —O—, forms a saturated or unsaturated heterocyclic group containing 3 or 4 carbon atoms and 0 or 1 additional nitrogen atoms wherein said saturated or unsaturated heterocyclic group is fused to a heterocyclic ring selected from the group consisting of dioxolane, dioxane, homodioxane, oxetane, tetrahydrofuran, dihydropyran, furan, oxazolidine, oxazole, isoxazole, oxazolidinone, oxathiolane, and 1,3-dioxolan-2-one and wherein the resulting fused ring is optionally substituted, in addition to the R² group, on any ring atom capable of substitution with 1 or 2 substituents selected from the group consisting of alkyl, alkoxy, substituted alkoxy, alkenyloxy, substituted alkenyloxy, halo, hydroxy, mono or dialkylamino. Preferably B is 2-pyridone or 6-pyrimidone that is fused to a heterocyclic ring selected from the group consisting of dioxolane, dioxane, homodioxane, oxetane, tetrahydrofuran, dihydropyran, furan, oxazolidine, oxazole, isoxazole, oxazolidinone, oxathiolane, and 1,3-dioxolan-2-one, and wherein the resulting fused ring is optionally substituted, in addition to the R² group, on any ring atom capable of substitution with 1 or 2 substituents selected from the group consisting of alkyl, alkoxy, substituted alkoxy, alkenyloxy, substituted alkenyloxy, halo, hydroxy, mono or dialkylamino, more preferably methyl, ethyl, propyl, methoxy, ethoxy, propoxy, butoxy, allyloxy, butenyloxy (wherein the methyl, ethyl, propyl, butyl, and allyl group in said methoxy, ethoxy, propoxy, butoxy, allyloxy, butenyloxy may be optionally substituted with one, two or three substituents selected from the group consisting of hydroxy, alkoxy, thiol, alkylthio, alkylsulfoxide, alkylsulfone, halo, alkylamino, dialkylamino, amino, aminoacyl, preferably, hydroxy, methoxy, ethoxy, methylthio, methylsulfane, methylsulfone, fluoro, methylamino, dimethylamino, amino, and acetylamino), chloro, bromo, hydroxy, methylamino, or dimethylamino. More preferably in the above rings R² is alkyl, preferably methyl.

In a preferred embodiment, in compound (Ib), C is either:

(a) a group wherein W', together with —C(═Z)N— where Z is —O—, forms an unsaturated heterocyclic group containing 2 to 4 carbon atoms and 0 to 2 additional nitrogen atoms and further the wherein the unsaturated heterocyclic group is optionally substituted, in addition to the R² group, with 1 or 2 substituents selected from the group consisting of alkyl, alkoxy, substituted alkoxy, alkenyloxy, substituted alkenyloxy, halo, hydroxy, mono or dialkylamino. Preferably C is 2-pyridon-1-yl or 6-pyrimidon-1-yl that is optionally substituted, in addition to the R² group, with 1 or 2 substituents selected from the group consisting of alkyl, alkoxy, substituted alkoxy, alkenyloxy, substituted alkenyloxy, halo, hydroxy, mono or dialkylamino, more preferably methyl, ethyl, propyl, methoxy, ethoxy, propoxy, butoxy, allyloxy, butenyloxy (wherein the methyl, ethyl, propyl, butyl, and allyl group in said methoxy, ethoxy, propoxy, butoxy, allyloxy, butenyloxy may be optionally substituted with one, two or three substituents selected from the group consisting of hydroxy, alkoxy, thiol, alkylthio, alkylsulfoxide, alkylsulfone, halo, alkylamino, dialkylamino, amino, aminoacyl, preferably, hydroxy, methoxy, ethoxy, methylthio, methylsulfane, methylsulfone, fluoro, methylamino, dimethylamino, amino, and acetylamino), chloro, bromo, hydroxy, methylamino, or dimethylamino. More preferably in the above rings R² is alkyl, preferably methyl; or (b) a group wherein W', together with —C(═Z)N— where Z is —O—, forms a saturated or unsaturated heterocyclic group containing 2 to 4 carbon atoms and 0 to 2 additional nitrogen atoms wherein said saturated or unsaturated heterocyclic group is fused to a heterocyclic ring selected from the group consisting of dioxolane, dioxane, homodioxane, oxetane, tetrahydrofuran, dihydropyran, furan, oxazolidine, oxazole, isoxazole, oxazolidinone, oxathiolane, and 1,3-dioxolan-2- one and wherein the resulting fused ring is optionally substituted, in addition to the $R^2$ group, on any ring atom capable of substitution with 1 or 2 substituents selected from the group consisting of alkyl, alkoxy, substituted alkoxy, alkenyloxy, substituted alkenyloxy, halo, hydroxy, mono or dialkylamino. Preferably C is 2-pyridon-1-yl or 6-pyrimidon-1-yl that is fused to a heterocyclic ring selected from the group consisting of dioxolane, dioxane, homodioxane, oxetane, tetrahydrofuran, dihydropyran, furan, oxazolidine, oxazole, isoxazole, oxazolidinone, oxathiolane, and 1,3-dioxolan-2-one, and wherein the resulting fused ring is optionally substituted, in addition to the $R^2$ group, on any ring atom capable of substitution with 1 or 2 substituents selected from the group consisting of alkyl, alkoxy, substituted alkoxy, alkenyloxy, substituted alkenyloxy, halo, hydroxy, mono or dialkylamino, more preferably methyl, ethyl, propyl, methoxy, ethoxy, propoxy, butoxy, allyloxy, butenyloxy (wherein the methyl, ethyl, propyl, butyl, and allyl group in said methoxy, ethoxy, propoxy, butoxy, allyloxy, butenyloxy may be optionally substituted with one, two or three substituents selected from the group consisting of hydroxy, alkoxy, thiol, alkylthio, alkylsulfoxide, alkylsulfone, halo, alkylamino, dialkylamino, amino, aminoacyl, preferably, hydroxy, methoxy, ethoxy, methylthio, methylsulfane, methylsulfone, fluoro, methylamino, dimethylamino, amino, and acetylamino), chloro, bromo, hydroxy, methylamino, or dimethylamino. More preferably in the above rings $R^2$ is alkyl, preferably methyl.

In another preferred embodiment, $Ar^1$ in compounds (Ia) and (Ib) is a heteroaryl group optionally substituted with 1 to 3 substituents selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen, preferably 1-oxo-1,2,5-thiadiazole, 1,1-dioxo-1,2,5-thiadiazole, 1,3,5-triazine, pyridazine, pyrimidine or pyrazine substituted with above substituents; more preferably pyridazine, pyrimidine or pyrazine wherein the pyridazine, pyrimidine or pyrazine ring is optionally substituted with 1 to 3 substituents selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen.

In yet another preferred embodiment, $Ar^2$ in compounds (Ia) and (Ib) is phenyl.

In the above preferred embodiments, a more preferred group of compounds is that wherein X is hydroxyl and $R^1$ is hydrogen.

In yet another preferred embodiment, this invention is directed to compounds of formula IIa, IIb, IIc, IId, or IIe:

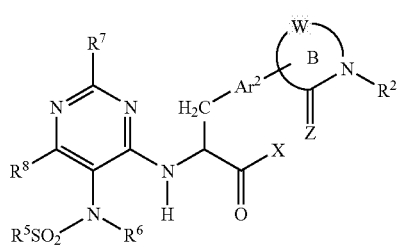

IIa

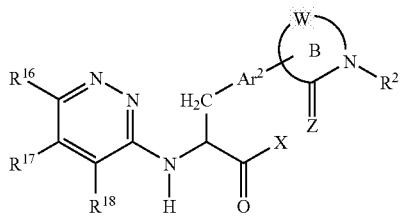

IIb

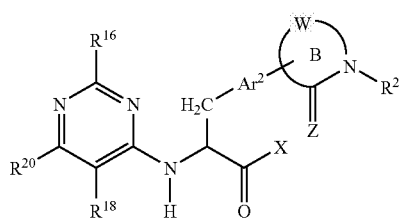

IIc

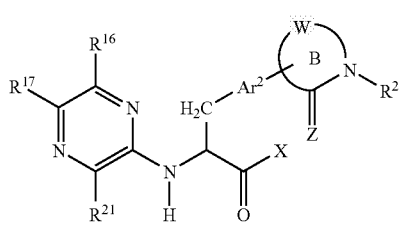

IId

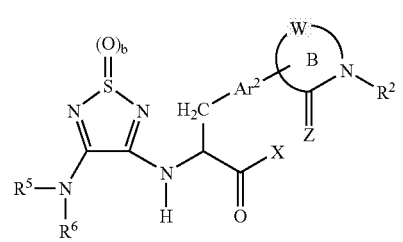

IIe wherein

X is hydroxyl or alkoxy;

$Ar^2$ is an aryl or heteroaryl group optionally substituted, in addition to ring B, with one or two substituent(s) selected from the group consisting of hydrogen, halogen, hydroxy, alkoxy, substituted alkoxy, acyloxy, substituted acyloxy, amino, alkylamino, substituted alkylamino, dialkylamino, substituted dialkylamino, acylamino, substituted acylamino, N-acyl-N-alkylamino, substituted N-acyl-N-alkylamino, (alkylsulfonyl)amino, substituted (alkylsulfonyl)amino, N-(alkylsulfonyl)-N-alkylamino, substituted N-(alkylsulfonyl)-N-alkylamino, alkyl, substituted alkyl, cycloalkyl, substituted cycloalkyl, alkenyl, substituted alkenyl, cycloalkenyl, substituted cycloalkenyl, alkynyl, substituted alkynyl, cyano, acyl, substituted acyl, carboxy, substituted carboxy, thiol, alkylthio, substituted alkylthio, alkylsulfoxy, substituted alkylsulfoxy, alkylsulfonyl, and substituted alkylsulfonyl;

$R^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

$R^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —SO$_2$R$^{10}$ where R$^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl;

R$^7$ and R$^8$ are independently selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and halogen;

R$^{16}$ and R$^{17}$ are independently selected from the group consisting of hydrogen, alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen; and R$^{18}$ is selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic and substituted heterocyclic;

R$^{20}$ is selected from the group consisting of hydrogen, alkyl, substituted alkyl, alkoxy, substituted alkoxy, cycloalkyl, substituted cycloalkyl, aryl, substituted aryl, heteroaryl, substituted heteroaryl, heterocyclic, substituted heterocyclic and halogen;

R$^{21}$ is selected from the group consisting of alkyl, substituted alkyl, alkoxy, substituted alkoxy, amino, substituted amino, cycloalkyl, substituted cycloalkyl, aryl, substituted aryl, heterocyclic and substituted heterocyclic;

b is 1 or 2; and

B is a group wherein W, together with —C(=Z)NR$^2$—, forms a saturated or unsaturated heterocyclic group containing 2 to 5 carbon atoms and 0 to 4 additional heteroatoms selected from the group consisting of nitrogen, oxygen, and —SO$_n$— (where n is 0 to 2) wherein said saturated or unsaturated heterocyclic group is optionally fused with one or two ring(s) structures selected from the group consisting of cycloalkyl, cycloalkenyl, heterocyclic, aryl and heteroaryl group to form a bi- or tri-fused ring system and further wherein said heterocyclic group and each of such ring structures are optionally substituted with 1 to 3 substituents selected from the group consisting of with one or two substituent(s) selected from the group consisting of hydrogen, halogen, hydroxy, alkoxy, substituted alkoxy, acyloxy, substituted acyloxy, amino, alkylamino, substituted alkylamino, dialkylamino, substituted dialkylamino, acylamino, substituted acylamino, N-acyl-N-alkylamino, substituted N-acyl-N-alkylamino, alkylene dioxy, (alkylsulfonyl)amino, substituted (alkylsulfonyl)amino, N-(alkylsulfonyl)-N-alkylamino, substituted N-(alkylsulfonyl)-N-alkylamino, alkyl, substituted alkyl, cycloalkyl, substituted cycloalkyl, alkenyl, substituted alkenyl, cycloalkenyl, substituted cycloalkenyl, alkynyl, substituted alkynyl, cyano, acyl, substituted acyl, carboxy, substituted carboxy, nitro, thiol, alkylthio, substituted alkylthio, alkylsulfoxy, substituted alkylsulfoxy, alkylsulfonyl, substituted alkylsulfonyl, aryl, substituted aryl, heteroaryl, substituted heteroaryl;

R$^2$ is selected from the group consisting of alkyl, substituted alkyl, aryl, substituted aryl, heteroaryl, substituted heteroaryl, cycloalkyl, substituted cycloalkyl, cycloalkenyl, and substituted cycloalkenyl; and and enantiomers, diastereomers and pharmaceutically acceptable salts thereof.

Preferably, the compound is selected from formula IIc, IId or IIe.

In the above compounds II(a-e), B is either:

(a) a group wherein W, together with —C(=Z)NR$^2$— where Z is —O—, forms an unsaturated heterocyclic group containing 2 to 4 carbon atoms and 0 to 2 additional nitrogen atoms and further the wherein the unsaturated heterocyclic group is optionally substituted, in addition to the R$^2$ group, with 1 or 2 substituents selected from the group consisting of alkyl, alkoxy, substituted alkoxy, alkenyloxy, substituted alkenyloxy, halo, hydroxy, mono or dialkylamino. Preferably B is 2-pyridone, (e.g., 2-pyridon-3-yl, 2-pyridon-4-yl, etc.,) or 6-pyrimidone (e.g., 6-pyrimidon-5-yl, etc.,) that is optionally substituted, in addition to the R$^2$ group, with 1 or 2 substituents selected from the group consisting of alkyl, alkoxy, substituted alkoxy, alkenyloxy, substituted alkenyloxy, halo, hydroxy, mono or dialkylamino, more preferably methyl, ethyl, propyl, methoxy, ethoxy, propoxy, butoxy, allyloxy, butenyloxy (wherein the methyl, ethyl, propyl, butyl, and allyl group in said methoxy, ethoxy, propoxy, butoxy, allyloxy, butenyloxy may be optionally substituted with one, two or three substituents selected from the group consisting of hydroxy, alkoxy, thiol, alkylthio, alkylsulfoxide, alkylsulfone, halo, alkylamino, dialkylamino, amino, aminoacyl, preferably, hydroxy, methoxy, ethoxy, methylthio, methylsulfane, methylsulfone, fluoro, methylamino, dimethylamino, amino, and acetylamino), chloro, bromo, hydroxy, methylamino, or dimethylamino. More preferably in the above rings R$^2$ is alkyl, preferably methyl; or (b) a group wherein W, together with —C(=Z)NR$^2$— where Z is —O—, forms a saturated or unsaturated heterocyclic group containing 2 to 4 carbon atoms and 0 to 2 additional nitrogen atoms wherein said saturated or unsaturated heterocyclic group is fused to a heterocyclic ring selected from the group consisting of dioxolane, dioxane, homodioxane, oxetane, tetrahydrofuran, dihydropyran, furan, oxazolidine, oxazole, isoxazole, oxazolidinone, oxathiolane, and 1,3-dioxolan-2-one and wherein the resulting fused ring is optionally substituted, in addition to the R$^2$ group, on any ring atom capable of substitution with 1 or 2 substituents selected from the group consisting of alkyl, alkoxy, substituted alkoxy, alkenyloxy, substituted alkenyloxy, halo, hydroxy, mono or dialkylamino. Preferably B is 2-pyridone or 6-pyrimidone that is fused to a heterocyclic ring selected from the group consisting of dioxolane, dioxane, homodioxane, oxetane, tetrahydrofuran, dihydropyran, furan, oxazolidine, oxazole, isoxazole, oxazolidinone, oxathiolane, and 1,3-dioxolan-2-one, and wherein the resulting fused ring is optionally substituted, in addition to the R$^2$ group, on any ring atom capable of substitution with 1 or 2 substituents selected from the group consisting of alkyl, alkoxy, substituted alkoxy, alkenyloxy, substituted alkenyloxy, halo, hydroxy, mono or dialkylamino, preferably methyl, ethyl, propyl, methoxy, ethoxy, propoxy, butoxy, allyloxy, butenyloxy (wherein the methyl, ethyl, propyl, butyl, and allyl group in said methoxy, ethoxy, propoxy, butoxy, allyloxy, butenyloxy may be optionally substituted with one, two or three substituents selected from the group consisting of hydroxy, alkoxy, thiol, alkylthio, alkylsulfoxide, alkylsulfone, halo, alkylamino, dialkylamino, amino, aminoacyl, preferably, hydroxy, methoxy, ethoxy, methylthio, methylsulfane, methylsulfone, fluoro, methylamino, dimethylamino, amino, and acetylamino), chloro, bromo, hydroxy, methylamino, or dimethylamino. More preferably in the above rings R$^2$ is alkyl, preferably methyl and X is hydroxyl.

In the above compounds II(a-e), Ar$^2$ is preferably phenyl.

Within the above preferred groups of II(a-e), a more preferred group of compounds is that wherein R$^5$ is selected from the group consisting of alkyl, substituted alkyl, aryl, substituted aryl, heterocyclic, substituted heterocylic, heteroaryl and substituted heteroaryl. Even more preferably R⁵ is selected from the group consisting of 4-methylphenyl, methyl, benzyl, n-butyl, n-hexyl, 4-chlorophenyl, 1-naphthyl, 2-naphthyl, 4-methoxyphenyl, phenyl, 2,4,6-trimethylphenyl, 2-(methoxycarbonyl)phenyl, 2-carboxyphenyl, 3,5-dichlorophenyl, 4-trifluoromethylphenyl, 3,4-dichlorophenyl, 3,4-dimethoxyphenyl, 4-(CH₃C(O)NH—)phenyl, 4-trifluoromethoxyphenyl, 4-cyanophenyl, isopropyl, 3,5-di-(trifluoromethyl)phenyl, 4-t-butylphenyl, 4-t-butoxyphenyl, 4-nitrophenyl, 2-thienyl, 1-N-methyl-3-methyl-5-chloropyrazol-4-yl, phenethyl, 1-N-methylimidazol-4-yl, 4-bromophenyl, 4-amidinophenyl, 4-methylamidinophenyl, 4-[CH₃SC(=NH)]phenyl, 5-chloro-2-thienyl, 2,5-dichloro-4-thienyl, 1-N-methyl-4-pyrazolyl, 2-thiazolyl, 5-methyl-1,3,4-thiadiazol-2-yl, 4-[H₂NC(S)]phenyl, 4-aminophenyl, 4-fluorophenyl, 2-fluorophenyl, 3-fluorophenyl, 3,5-difluorophenyl, pyridin-3-yl, pyrimidin-2-yl, 4-(3'-dimethylamino-n-propoxy)-phenyl, and 1-methylpyrazol-4-yl;

R¹⁶ is substituted amino,

R⁶, R¹⁷ and/or R²⁰ are hydrogen; and

R¹⁸ and/or R²¹ are alkyl, substituted alkyl, aryl, or substituted aryl.

In a second aspect, this invention provides pharmaceutical compositions comprising a pharmaceutically acceptable carrier and a therapeutically effective amount of the compounds defined herein.

In a third aspect, this invention is directed to a method for treating a disease mediated by VLA-4 in a patient, which method comprises administering a pharmaceutical composition comprising a pharmaceutically acceptable carrier and a therapeutically effective amount of compounds defined herein.

In the above compounds, when X is other than —OH or pharmaceutical salts thereof, X is preferably a substituent which will convert (e.g., hydrolyze, metabolize, etc.) in vivo to a compound where X is —OH or a salt thereof. Accordingly, suitable X groups are any art recognized pharmaceutically acceptable groups which will hydrolyze or otherwise convert in vivo to a hydroxyl group or a salt thereof including, by way of example, esters (X is alkoxy, substituted alkoxy, cycloalkoxy, substituted cycloalkoxy, alkenoxy, substituted alkenoxy, cycloalkenoxy, substituted cycloalkenoxy, aryloxy, substituted aryloxy, heteroaryloxy, substituted heteroaryloxy, heterocyclooxy, substituted heterocyclooxy, and the like).

This invention also provides methods for binding VLA-4 in a biological sample which method comprises contacting the biological sample with a compound of this invention under conditions wherein said compound binds to VLA-4.

The compounds and pharmaceutical compositions of this invention are useful for treating disease conditions mediated by VLA-4 or leucocyte adhesion. Such disease conditions include, by way of example, asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Other disease conditions include, but are not limited to, inflammatory conditions such as erythema nodosum, allergic conjunctivitis, optic neuritis, uveitis, allergic rhinitis, Ankylosing spondylitis, psoriatic arthritis, vasculitis, Reiter's syndrome, systemic lupus erythematosus, progressive systemic sclerosis, polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

In a preferred embodiment, the disease condition mediated by VLA-4 is an inflammatory disease.

Preferred compounds of this invention include those set forth in the Table below:

TABLE I

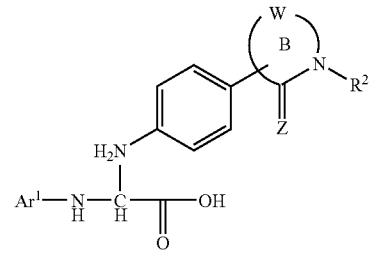

| Cpd # | A | B |
|---|---|---|
| 1 | [2-(C₂H₅)₂N-5-CF₃CH₂]pyrimidin-4-yl | 1-CH₃4-CH₃O-2-pyridon-3-yl |
| 2 | [2-(C₂H₅)₂N-5-CF₃CH₂]pyrimidin-4-yl | 1-C₂H₅-4-CH₃O-2-pyridon-3-yl |
| 3 | [2-(C₂H₅)₂N-5-CF₃CH₂]pyrimidin-4-yl | 1-n-C₃H₇-4-CH₃O-2-pyridon-3-yl |
| 4 | [2-(C₂H₅)₂N-5-CF₃CH₂]pyrimidin-4-yl | 1-i-C₃H₇-4-CH₃O-2-pyridon-3-yl |
| 5 | [2-(C₂H₅)₂N-5-CF₃CH₂]pyrimidin-4-yl | 1-CH₃-4-CH₃O-6-pyrimidon-5-yl |
| 6 | [2-(C₂H₅)₂N-5-CF₃CH₂]pyrimidin-4-yl | 1-C₂H₅-4-CH₃O-6-pyrimidon-5-yl |
| 7 | [2-(C₂H₅)₂N-5-CF₃CH₂]pyrimidin-4-yl | 1-n-C₃H₇-4-CH₃O-6-pyrimidon-5-yl |
| 8 | [2-(C₂H₅)₂N-5-CF₃CH₂]pyrimidin-4-yl | 1-i-C₃H₇-4-CH₃O-6-pyrimidon-5-yl |
| 9 | [2-(C₂H₅)₂N-5-(CH₃)₂CH]pyrimidin-4-yl | 1-CH₃-4-CH₃O-2-pyridon-3-yl |
| 10 | [2-(C₂H₅)₂N-5-(CH₃)₂CH]pyrimidin-4-yl | 1-C₂H₅-4-CH₃O-2-pyridon-3-yl |
| 11 | [2-(C₂H₅)₂N-5-(CH₃)₂CH]pyrimidin-4-yl | 1-n-C₃H₇-4-CH₃O-2-pyridon-3-yl |
| 12 | [2-(C₂H₅)₂N-5-(CH₃)₂CH]pyrimidin-4-yl | 1-i-C₃H₇-4-CH₃O-2-pyridon-3-yl |
| 13 | [2-(C₂H₅)₂N-5-(CH₃)₂CH]pyrimidin-4-yl | 1-CH₃-4-CH₃O-6-pyrimidon-5-yl |
| 14 | [2-(C₂H₅)₂N-5-(CH₃)₂CH]pyrimidin-4-yl | 1-C₂H₅-4-CH₃O-6-pyrimidon-5-yl |
| 15 | [2-(C₂H₅)₂N-5-(CH₃)₂CH]pyrimidin-4-yl | 1-n-C₃H₇-4-CH₃O-6-pyrimidon-5-yl |
| 16 | [2-(C₂H₅)₂N-5-(CH₃)₂CH]pyrimidin-4-yl | 1-i-C₃H₇-4-CH₃O-6-pyrimidon-5-yl |
| 17 | [2-(C₂H₅)₂N-5-(CH₃CH₂)₂CH]-pyrimidin-4-yl | 1-i-C₃H₇-4-CH₃O-2-pyridon-3-yl |
| 18 | [2-(C₂H₅)₂N-5-(CH₃CH₂)₂CH]-pyrimidin-4-yl | 1-CH₃-4-CH₃O-2-pyridon-3-yl |
| 19 | [2-(C₂H₅)₂N-5-(CH₃CH₂)₂CH]-pyrimidin-4-yl | 1-n-C₂H₅-4-CH₃O-2-pyridon-3-yl |
| 20 | [2-(C₂H₅)₂N-5-(CH₃CH₂)₂CH]-pyrimidin-4-yl | 1-i-C₂H₅-4-CH₃O-2-pyridon-3-yl |
| 21 | [2-(C₂H₅)₂N-5-(CH₃CH₂)₂CH]-pyrimidin-4-yl | 1-CH₃-4-CH₃O-6-pyrimidon-5-yl |
| 22 | [2-(C₂H₅)₂N-5-(CH₃CH₂)₂CH]-pyrimidin-4-yl | 1-C₂H₅-4-CH₃O-6-pyrimidon-5-yl |

TABLE I-continued

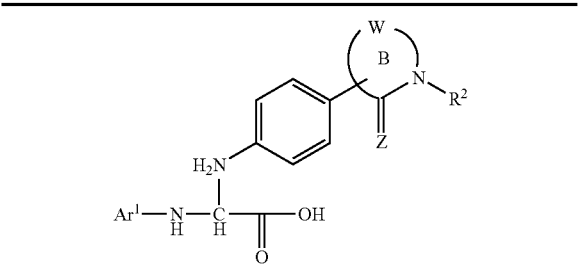

| Cpd # | A | B |
|---|---|---|
| 23 | [2-(C₂H₅)₂N-5-(CH₃CH₂)₂CH]-pyrimidin-4-yl | 1-n-C₃H₇-4-CH₃O-6-pyrimidon-5-yl |
| 24 | [2-(C₂H₅)₂N-5-(CH₃CH₂)₂CH]-pyrimidin-4-yl | 1-i-C₃H₇-4-CH₃O-6-pyrimidon-5-yl |
| 25 | [2-(C₂H₅)₂N-5-(3,5-diCH₃isoxazol-4-yl)]pyrimidin-4-yl | 1-CH₃-4-CH₃O-2-pyridon-3-yl |
| 26 | [2-(C₂H₅)₂N-5-(3,5-diCH₃isoxazol-4-yl)]pyrimidin-4-yl | 1-C₂H₅-4-CH₃O-2-pyridon-3-yl |
| 27 | [2-(C₂H₅)₂N-5-(3,5-diCH₃isoxazol-4-yl)]pyrimidin-4-yl | 1-n-C₃H₇-4-CH₃O-2-pyridon-3-yl |
| 28 | [2-(C₂H₅)₂N-5-(3,5-diCH₃isoxazol-4-yl)]pyrimidin-4-yl | 1-i-C₃H₇-4-CH₃O-2-pyridon-3-yl |
| 29 | [2-(C₂H₅)₂N-5-(3,5-diCH₃isoxazol-4-yl)]pyrimidin-4-yl | 1-CH₃-4-CH₃O-6-pyrimidon-5-yl |
| 30 | [2-(C₂H₅)₂N-5-(3,5-diCH₃isoxazol-4-yl)]pyrimidin-4-yl | 1-C₂H₅-4-CH₃O-6-pyrimidon-5-yl |
| 31 | [2-(C₂H₅)₂N-5-(3,5-diCH₃isoxazol-4-yl)]pyrimidin-4-yl | 1-n-C₃H₇-4-CH₃O-6-pyrimidon-5-yl |
| 32 | [2-(C₂H₅)₂N-5-(3,5-diCH₃isoxazol-4-yl)]pyrimidin-4-yl | 1-i-C₃H₇-4-CH₃O-6-pyrimidon-5-yl |
| 33 | [2-(C₂H₅)₂N-5-(1,3,5-triCH₃pyrazol-4-yl)]pyrimidin-4-yl | 1-CH₃-4-CH₃O-2-pyridon-3-yl |
| 34 | [2-(C₂H₅)₂N-5-(1,3,5-triCH₃pyrazol-4-yl)]pyrimidin-4-yl | 1-C₂H₅-4-CH₃O-2-pyridon-3-yl |
| 35 | [2-(C₂H₅)₂N-5-(1,3,5-triCH₃pyrazol-4-yl)]pyrimidin-4-yl | 1-n-C₃H₇-4-CH₃O-2-pyridon-3-yl |
| 36 | [2-(C₂H₅)₂N-5-(1,3,5-triCH₃pyrazol-4-yl)]pyrimidin-4-yl | 1-i-C₃H₇-4-CH₃O-2-pyridon-3-yl |
| 37 | [2-(C₂H₅)₂N-5-(1,3,5-triCH₃pyrazol-4-yl)]pyrimidin-4-yl | 1-CH₃-4-CH₃O-6-pyrimidon-5-yl |
| 38 | [2-(C₂H₅)₂N-5-(1,3,5-triCH₃pyrazol-4-yl)]pyrimidin-4-yl | 1-C₂H₅-4-CH₃O-6-pyrimidon-5-yl |
| 39 | [2-(C₂H₅)₂N-5-(1,3,5-triCH₃pyrazol-4-yl)]pyrimidin-4-yl | 1-n-C₃H₇-4-CH₃O-6-pyrimidon-5-yl |
| 40 | [2-(C₂H₅)₂N-5-(1,3,5-triCH₃pyrazol-4-yl)]pyrimidin-4-yl | 1-i-C₃H₇-4-CH₃O-6-pyrimidon-5-yl |
| 41 | [2-(C₂H₅)₂N-5-(3,5-diCH₃isothiazol-4-yl)]pyrimidin-4-yl | 1-CH₃-4-CH₃O-2-pyridon-3-yl |
| 42 | [2-(C₂H₅)₂N-5-(3,5-diCH₃isothiazol-4-yl)]pyrimidin-4-yl | 1-C₂H₅-4-CH₃O-2-pyridon-3-yl |
| 43 | [2-(C₂H₅)₂N-5-(3,5-diCH₃isothiazol-4-yl)]pyrimidin-4-yl | 1-n-C₃H₇-4-CH₃O-2-pyridon-3-yl |

TABLE I-continued

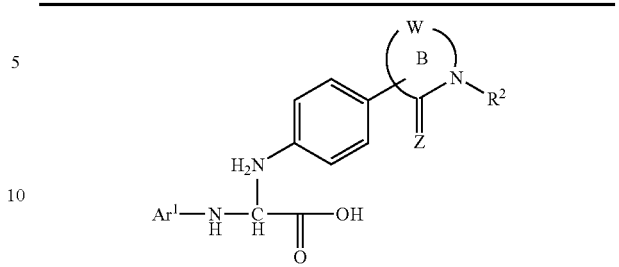

| Cpd # | A | B |
|---|---|---|
| 44 | [2-(C₂H₅)₂N-5-(3,5-diCH₃isothiazol-4-yl)]pyrimidin-4-yl | 1-i-C₃H₇-4-CH₃O-2-pyridon-3-yl |
| 45 | [2-(C₂H₅)₂N-5-(3,5-diCH₃isothiazol-4-yl)]pyrimidin-4-yl | 1-CH₃-4-CH₃O-6-pyrimidon-5-yl |
| 46 | [2-(C₂H₅)₂N-5-(3,5-diCH₃isothiazol-4-yl)]pyrimidin-4-yl | 1-C₂H₅-4-CH₃O-6-pyrimidon-5-yl |
| 47 | [2-(C₂H₅)₂N-5-(3,5-diCH₃isothiazol-4-yl)]pyrimidin-4-yl | 1-n-C₃H₇-4-CH₃O-6-pyrimidon-5-yl |
| 48 | [2-(C₂H₅)₂N-5-(3,5-diCH₃isothiazol-4-yl)]pyrimidin-4-yl | 1-i-C₃H₇-4-CH₃O-6-pyrimidon-5-yl | and are named as follows:

N-(2-(N,N-diethylamino)-5-(2,2,2-trifluoroethyl)pyrimidin-4-yl)-L-4'-(1-methyl-4-methoxy-2-pyridon-3-yl)phenylalanine;

N-(2-(N,N-diethylamino)-5-(2,2,2-trifluoroethyl)pyrimidin-4-yl)-L-4'-(1-ethyl-4-methoxy-2-pyridon-3-yl)phenylalanine;

N-(2-(N,N-diethylamino)-5-(2,2,2-trifluoroethyl)pyrimidin-4-yl)-L-4'-(1-propyl-4-methoxy-2-pyridon-3-yl)phenylalanine;

N-(2-(N,N-diethylamino)-5-(2,2,2-trifluoroethyl)pyrimidin-4-yl)-L-4'-(1-isopropyl-4-methoxy-2-pyridon-3-yl)phenylalanine;

N-(2-(N,N-diethylamino)-5-(2,2,2-trifluoroethyl)pyrimidin-4-yl)-L-4'-(1-methyl-4-methoxy-6-pyrimidon-5-yl)phenylalanine;

N-(2-(N,N-diethylamino)-5-(2,2,2-trifluoroethyl)pyrimidin-4-yl)-L-4'-(1-ethyl-4-methoxy-6-pyrimidon-5-yl)phenylalanine;

N-(2-(N,N-diethylamino)-5-(2,2,2-trifluoroethyl)pyrimidin-4-yl)-L-4'-(1-propyl-4-methoxy-6-pyrimidon-5-yl)phenylalanine;

N-(2-(N,N-diethylamino)-5-(2,2,2-trifluoroethyl)pyrimidin-4-yl)-L-4'-(1-isopropyl-4-methoxy-6-pyrimidon-5-yl)phenylalanine;

N-(2-(N,N-diethylamino)-5-(2-methylpropyl)pyrimidin-4-yl)-L-4'-(1-methyl-4-methoxy-2-pyridon-3-yl)phenylalanine;

N-(2-(N,N-diethylamino)-5-(2-methylpropyl)pyrimidin-4-yl)-L-4'-(1-ethyl-4-methoxy-2-pyridon-3-yl)phenylalanine;

N-(2-(N,N-diethylamino)-5-(2-methylpropyl)pyrimidin-4-yl)-L-4'-(1-propyl-4-methoxy-2-pyridon-3-yl)phenylalanine;

N-(2-(N,N-diethylamino)-5-(2-methylpropyl)pyrimidin-4-yl)-L-4'-(1-isopropyl-4-methoxy-2-pyridon-3-yl)phenylalanine;

N-(2-(N,N-diethylamino)-5-(2-methylpropyl)pyrimidin-4-yl)-L-4'-(1-methyl-4-methoxy-6-pyrimidon-5-yl)phenylalanine;

N-(2-(N,N-diethylamino)-5-(2-methylpropyl)pyrimidin-4-yl)-L-4'-(1-ethyl-4-methoxy-6-pyrimidon-5-yl)phenylalanine;

N-(2-(N,N-diethylamino)-5-(2-methylpropyl)pyrimidin-4-yl)-L-4'-(1-propyl-4-methoxy-6-pyrimidon-5-yl)phenylalanine;

N-(2-(N,N-diethylamino)-5-(2-methylpropyl)pyrimidin-4-yl)-L-4'-(1-isopropyl-4-methoxy-6-pyrimidon-5-yl)phenylalanine;

N-(2-(N,N-diethylamino)-5-(1-ethylpropyl)pyrimidin-4-yl)-L-4'-(1-methyl-4-methoxy-2-pyridon-3-yl)phenylalanine;

N-(2-(N,N-diethylamino)-5-(1-ethylpropyl)pyrimidin-4-yl)-L-4'-(1-ethyl-4-methoxy-2-pyridon-3-yl)phenylalanine;

N-(2-(N,N-diethylamino)-5-(1-ethylpropyl)pyrimidin-4-yl)-L-4'-(1-propyl-4-methoxy-2-pyridon-3-yl)phenylalanine;

N-(2-(N,N-diethylamino)-5-(1-ethylpropyl)pyrimidin-4-yl)-L-4'-(1-isopropyl-4-methoxy-2-pyridon-3-yl)phenylalanine;

N-(2-(N,N-diethyl-amino)-5-(1-ethylpropyl)pyrimidin-4-yl)-L-4'-(1-methyl-4-methoxy-6-pyrimidon-5-yl)phenylalanine;

N-(2-(N,N-diethylamino)-5-(1-ethylpropyl)pyrimidin-4-yl)-L-4'-(1-ethyl-4-methoxy-6-pyrimidon-5-yl)phenylalanine;

N-(2-(N,N-diethylamino)-5-(1-ethylpropyl)pyrimidin-4-yl)-L-4'-(1-propyl-4-methoxy-6-pyrimidon-5-yl)phenylalanine;

N-(2-(N,N-diethylamino)-5-(1-ethylpropyl)pyrimidin-4-yl)-L-4'-(1-isopropyl-4-methoxy-6-pyrimidon-5-yl)phenylalanine;

N-(2-(N,N-diethylamino)-5-(3,5-dimethylisoxazol-4-yl)pyrimidin-4-yl)-L-4'-(1-methyl-4-methoxy-2-pyridon-3-yl)phenylalanine;

N-(2-(N,N-diethylamino)-5-(3,5-dimethylisoxazol-4-yl)pyrimidin-4-yl)-L-4'-(1-ethyl-4-methoxy-2-pyridon-3-yl)phenylalanine;

N-(2-(N,N-diethylamino)-5-(3,5-dimethylisoxazol-4-yl)pyrimidin-4-yl)-L-4'-(1-propyl-4-methoxy-2-pyridon-3-yl)phenylalanine;

N-(2-(N,N-diethylamino)-5-(3,5-dimethylisoxazol-4-yl)pyrimidin-4-yl)-L-4'-(1-isopropyl-4-methoxy-2-pyridon-3-yl)phenylalanine;

N-(2-(N,N-diethylamino)-5-(3,5-dimethylisoxazol-4-yl)pyrimidin-4-yl)-L-4'-(1-methyl-4-methoxy-6-pyrimidon-5-yl)phenylalanine;

N-(2-(N,N-diethylamino)-5-(3,5-dimethylisoxazol-4-yl)pyrimidin-4-yl)-L-4'-(1-ethyl-4-methoxy-6-pyrimidon-5-yl)phenylalanine;

N-(2-(N,N-diethylamino)-5-(3,5-dimethylisoxazol-4-yl)pyrimidin-4-yl)-L-4'-(1-propyl-4-methoxy-6-pyrimidon-5-yl)phenylalanine;

N-(2-(N,N-diethylamino)-5-(3,5-dimethylisoxazol-4-yl)pyrimidin-4-yl)-L-4'-(1-isopropyl-4-methoxy-6-pyrimidon-5-yl)phenylalanine;

N-(2-(N,N-diethylamino)-5-(1,3,5-trimethylpyrazol-4-yl)pyrimidin-4-yl)-L-4'-(1-methyl-4-methoxy-2-pyridon-3-yl)phenylalanine;

N-(2-(N,N-diethylamino)-5-(1,3,5-trimethylpyrazol-4-yl)pyrimidin-4-yl)-L-4'-(1-ethyl-4-methoxy-2-pyridon-3-yl)phenylalanine;

N-(2-(N,N-diethylamino)-5-(1,3,5-trimethylpyrazol-4-yl)pyrimidin-4-yl)-L-4'-(1-propyl-4-methoxy-2-pyridon-3-yl)phenylalanine;

N-(2-(N,N-diethylamino)-5-(1,3,5-trimethylpyrazol-4-yl)pyrimidin-4-yl)-L-4'-(1-isopropyl-4-methoxy-2-pyridon-3-yl)phenylalanine;

N-(2-(N,N-diethylamino)-5-(1,3,5-trimethylpyrazol-4-yl)pyrimidin-4-yl)-L-4'-(1-methyl-4-methoxy-6-pyrimidon-5-yl)phenylalanine;

N-(2-(N,N-diethylamino)-5-(1,3,5-trimethylpyrazol-4-yl)pyrimidin-4-yl)-L-4'-(1-ethyl-4-methoxy-6-pyrimidon-5-yl)phenylalanine;

N-(2-(N,N-diethylamino)-5-(1,3,5-trimethylpyrazol-4-yl)pyrimidin-4-yl)-L-4'-(1-propyl-4-methoxy-6-pyrimidon-5-yl)phenylalanine;

N-(2-(N,N-diethylamino)-5-(1,3,5-trimethylpyrazol-4-yl)pyrimidin-4-yl)-L-4'-(1-isopropyl-4-methoxy-6-pyrimidon-5-yl)phenylalanine;

N-(2-(N,N-diethylamino)-5-(3,5-dimethylisothiazol-4-yl)pyrimidin-4-yl)-L-4'-(1-methyl-4-methoxy-2-pyridon-3-yl)phenylalanine;

N-(2-(N,N-diethylamino)-5-(3,5-dimethylisothiazol-4-yl)pyrimidin-4-yl)-L-4'-(1-ethyl-4-methoxy-2-pyridon-3-yl)phenylalanine;

N-(2-(N,N-diethylamino)-5-(3,5-dimethylisothiazol-4-yl)pyrimidin-4-yl)-L-4'-(1-propyl-4-methoxy-2-pyridon-3-yl)phenylalanine;

N-(2-(N,N-diethylamino)-5-(3,5-dimethylisothiazol-4-yl)pyrimidin-4-yl)-L-4'-(1-isopropyl-4-methoxy-2-pyridon-3-yl)phenylalanine;

N-(2-(N,N-diethylamino)-5-(3,5-dimethylisothiazol-4-yl)pyrimidin-4-yl)-L-4'-(1-methyl-4-methoxy-6-pyrimidon-5-yl)phenylalanine;

N-(2-(N,N-diethylamino)-5-(3,5-dimethylisothiazol-4-yl)pyrimidin-4-yl)-L-4'-(1-ethyl-4-methoxy-6-pyrimidon-5-yl)phenylalanine;

N-(2-(N,N-diethylamino)-5-(3,5-dimethylisothiazol-4-yl)pyrimidin-4-yl)-L-4'-(1-propyl-4-methoxy-6-pyrimidon-5-yl)phenylalanine; and N-(2-(N,N-diethylamino)-5-(3,5-dimethylisothiazol-4-yl)pyrimidin-4-yl)-L-4'-(1-isopropyl-4-methoxy-6-pyrimidon-5-yl)phenylalanine.

DETAILED DESCRIPTION OF THE INVENTION

As above, this invention relates to compounds which inhibit leukocyte adhesion and, in particular, leukocyte adhesion mediated by VLA-4. However, prior to describing this invention in further detail, the following terms will first be defined.

DEFINITIONS

As used herein, "alkyl" refers to alkyl groups preferably having from 1 to 10 carbon atoms and more preferably 1 to 6 carbon atoms. This term is exemplified by groups such as methyl, t-butyl, n-heptyl, octyl and the like.

"Substituted alkyl" refers to an alkyl group, preferably of from 1 to 10 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone; thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

"Alkenoxy" refers to the group "alkenyl-O—".

"Substituted alkenoxy" refers to the group "substituted alkenyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxysulfonyl" refers to the groups alkyl-SO$_2$O—, substituted alkyl-SO$_2$O—, alkenyl-SO$_2$O—, substituted alkenyl-SO$_2$O—, alkynyl-SO$_2$O—, substituted alkynyl-SO$_2$O—, aryl-SO$_2$O—, substituted aryl-SO$_2$O—, cycloalkyl-SO$_2$O—, substituted cycloalkyl-SO$_2$O—, heteroaryl-SO$_2$O—, substituted heteroaryl-SO$_2$O—, heterocyclic-SO$_2$O—, and substituted heterocyclic-SO$_2$O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 10 carbon atoms and more preferably 2 to 6 carbon atoms and having at least 1 and preferably from 1-2 sites of alkenyl unsaturation.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$- alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkenyl groups having amino groups blocked by conventional blocking groups such as Boc, Cbz, formyl, and the like or alkenyl/substituted alkenyl groups substituted with —SO₂-alkyl, —SO₂-substituted alkyl, —SO₂-alkenyl, —SO₂-substituted alkenyl, —SO₂-cycloalkyl, —SO₂-substituted-cycloalkyl, —SO₂-aryl, —SO₂-substituted aryl, —SO₂-heteroaryl, —SO₂-substituted heteroaryl, —SO₂-heterocyclic, —SO₂-substituted heterocyclic and —SO₂NRR where R is hydrogen or alkyl.

"Alkynyl" refers to alkynyl group preferably having from 2 to 10 carbon atoms and more preferably 3 to 6 carbon atoms and having at least 1 and preferably from 1-2 sites of alkynyl unsaturation.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalklyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR where R is hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO₂-alkyl, —SO₂-substituted alkyl, —SO₂-alkenyl, —SO₂-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclic, —SO₂-substituted heterocyclic and —SO₂NRR where R is hydrogen or alkyl.

"Amidino" refers to the group H₂NC(=NH)— and the term "alkylamidino" refers to compounds having 1 to 3 alkyl groups (e.g., alkylHNC(=NH)—).

"Thioamidino" refers to the group RSC(=NH)— where R is hydrogen or alkyl.

"Amino" refers to the group —NH₂.

"Substituted amino" refers to the group —NRR, where each R group is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, —SO₂-alkyl, —SO₂-substituted alkyl, —SO₂-alkenyl, —SO₂-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclic, —SO₂-substituted heterocyclic, provided that both R groups are not hydrogen; or the R groups can be joined together with the nitrogen atom to form a heterocyclic or substituted heterocyclic ring.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the groups —NRSO₂alkyl, —NRSO₂substituted alkyl, —NRSO₂cycloalkyl, —NRSO₂substituted cycloalkyl, —NRSO₂alkenyl, —NRSO₂substituted alkenyl, —NRSO₂alkynyl, —NRSO₂substituted alkynyl, —NRSO₂aryl, —NRSO₂substituted aryl, —NRSO₂heteroaryl, —NRSO₂substituted heteroaryl, —NRSO₂heterocyclic, and —NRSO₂substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)O-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the groups —NRSO$_2$O-alkyl, —NRSO$_2$O-substituted alkyl, —NRSO$_2$O-alkenyl, —NRSO$_2$O-substituted alkenyl, —NRSO$_2$O-alkynyl, —NRSO$_2$O-substituted alkynyl, —NRSO$_2$O-cycloalkyl, —NRSO$_2$O-substituted cycloalkyl, —NRSO$_2$O-aryl, —NRSO$_2$O-substituted aryl, —NRSO$_2$O-heteroaryl, —NRSO$_2$O-substituted heteroaryl, —NRSO$_2$O-heterocyclic, and —NRSO$_2$O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" refers to the groups —OC(O)NH$_2$, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NH$_2$, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxysulfonylamino" refers to the groups —OSO$_2$NH$_2$, —OSO$_2$NRR, —OSO$_2$NR-alkyl, —OSO$_2$NR-substituted alkyl, —OSO$_2$NR-alkenyl, —OSO$_2$NR-substituted alkenyl, —OSO$_2$NR-alkynyl, —OSO$_2$NR-substituted alkynyl, —OSO$_2$NR-cycloalkyl, —OSO$_2$NR-substituted cycloalkyl, —OSO$_2$NR-aryl, —OSO$_2$NR-substituted aryl, —OSO$_2$NR-heteroaryl, —OSO$_2$NR-substituted heteroaryl, —OSO$_2$NR-heterocyclic, and —OSO$_2$NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the groups —NRSO$_2$NRR, —NRSO$_2$NR-alkyl, —NRSO$_2$NR-substituted alkyl, —NRSO$_2$NR-alkenyl, —NRSO$_2$NR-substituted alkenyl, —NRSO$_2$NR-alkynyl, —NRSO$_2$NR-substituted alkynyl, —NRSO$_2$NR-aryl, —NRSO$_2$NR-substituted aryl, —NRSO$_2$NR-cycloalkyl, —NRSO$_2$NR-substituted cycloalkyl, —NRSO$_2$NR-heteroaryl, and —NRSO$_2$NR-substituted heteroaryl, —NRSO$_2$NR-heterocyclic, and —NRSO$_2$NR-substituted heterocyclic, where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like). Preferred aryls include phenyl and naphthyl.

Substituted aryl refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Aryloxy" refers to the group aryl-O— which includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclohexyl, cyclooctyl and the like. Excluded from this definition are multi-ring alkyl groups such as adamantanyl, etc.

"Cycloalkenyl" refers to cyclic alkenyl groups of from 3 to 8 carbon atoms having single or multiple unsaturation but which are not aromatic.

"Substituted cycloalkyl" and "substituted cycloalkenyl" refer to a cycloalkyl and cycloalkenyl groups, preferably of from 3 to 8 carbon atoms, having from 1 to 5 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Cycloalkoxy" refers to —O-cycloalkyl groups.

"Substituted cycloalkoxy" refers to —O-substituted cycloalkyl groups.

"Cycloalkenoxy" refers to —O-cycloalkenyl groups.

"Substituted cycloalkenoxy" refers to —O-substituted cycloalkenyl groups.

"Guanidino" refers to the groups —NRC(=NR)NRR, —NRC(=NR)NR-alkyl, —NRC(=NR)NR-substituted alkyl, —NRC(=NR)NR-alkenyl, —NRC(=NR)NR-substituted alkenyl, —NRC(=NR)NR-alkynyl, —NRC(=NR)NR-substituted alkynyl, —NRC(=NR)NR-aryl, —NRC(=NR)NR-substituted aryl, —NRC(=NR)NR-cycloalkyl, —NRC(=NR)NR-heteroaryl, —NRC(=NR)NR-substituted heteroaryl, —NRC(=NR)NR-heterocyclic, and —NRC(=NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Guanidinosulfone" refers to the groups —NRC(=NR)NRSO$_2$-alkyl, —NRC(=NR)NRSO$_2$-substituted alkyl, —NRC(=NR)NRSO$_2$-alkenyl, —NRC(=NR)NRSO$_2$-substituted alkenyl, —NRC(=NR)NRSO$_2$-alkynyl, —NRC(=NR)NRSO$_2$-substituted alkynyl, —NRC(=NR)NRSO$_2$-aryl, —NRC(=NR)NRSO$_2$-substituted aryl, —NRC(=NR)NRSO$_2$-cycloalkyl, —NRC(=NR)NRSO$_2$-substituted cycloalkyl, —NRC(=NR)NRSO$_2$-heteroaryl, and —NRC(=NR)NRSO$_2$-substituted heteroaryl, —NRC(=NR)NRSO$_2$-heterocyclic, and —NRC(=NR)NRSO$_2$-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is either chloro or bromo.

"Heteroaryl" refers to an aromatic carbocyclic group of from 2 to 10 carbon atoms and 1 to 4 heteroatoms selected from oxygen, nitrogen and sulfur within the ring or oxides thereof. Such heteroaryl groups can have a single ring (e.g., pyridyl or furyl) or multiple condensed rings (e.g., indolizinyl or benzothienyl). Additionally, the heteroatoms of the heteroaryl group may be oxidized, i.e., to form pyridine N-oxides or 1,1-dioxo-1,2,5-thiadiazoles and the like. Preferred heteroaryls include pyridyl, pyrrolyl, indolyl, furyl, pyridazinyl, pyrimidinyl, pyrazinyl, 1-oxo-1,2,5-thiadiazolyl and 1,1-dioxo-1,2,5-thiadiazolyl. The term "heteroaryl having two nitrogen atoms in the heteroaryl ring" refers to a heteroaryl group having two, and only two, nitrogen atoms in the heteroaryl ring and optionally containing 1 or 2 other heteroatoms in the heteroaryl ring, such as oxygen or sulfur "Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —$SO_2NRR$ where R is hydrogen or alkyl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from nitrogen, sulfur or oxygen within the ring wherein, in fused ring systems, one or more of the rings can be aryl or heteroaryl.

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic and —$SO_2NRR$ where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, thiomorpholino, piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Thiol" refers to the group —SH.

"Thioalkyl" or "alkylthio" refers to the groups —S-alkyl

"Substituted thioalkyl" refers to the group —S-substituted alkyl.

"Alkylsulfoxy" refers to the group —SO-alkyl.

"Substituted alkylsulfoxy" refers to the group —SO-substituted alkyl.

"Alkylsulfonyl" refers to the group —$SO_2$-alkyl.

"Substituted alkylsulfonyl" refers to the group —$SO_2$-substituted alkyl.

"Thiocycloalkyl" refers to the groups —S-cycloalkyl.

"Substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Alkylamino" or "substituted alkylamino" refers to the group —NHR wherein R is alkyl or substituted alkyl groups respectively as defined above.

"Dialkylamino" or "substituted dialkylamino" refers to the group —NRR wherein each R is alkyl or substituted alkyl groups respectively as defined above.

"Alkylsulfonylamino" or "substituted alkylsulfonylamino" refers to the group —$NHSO_2R$ wherein R is alkyl or substituted alkyl groups respectively as defined above.

"N-Alkylsulfonyl-N-alkylamino" refers to the group —$NRSO_2R^a$ wherein R and $R^a$ are independently alkyl wherein alkyl is as defined above.

"Substituted N-alkylsulfonyl-N-alkylamino" refers to the group —$NRSO_2R^a$ wherein R and $R^a$ are independently alkyl or substituted alkyl groups wherein substituted alkyl is as defined above.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

In a preferred method of synthesis, the compounds, (Ia) or (Ib) of this invention are prepared by coupling an amino acid derivative of the formula (a) or (b) respectively:

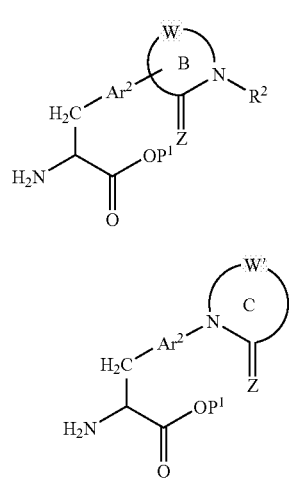

where $Ar^2$, ring B, C, $R^1$, $R^2$ are as defined herein and $P^1$ is a carboxylic acid protecting group (such as an alkyl group, i.e. methyl, ethyl and the like), with a suitably functionalized heteroaryl or heterocyclic intermediate. For example, such coupling reactions may be performed by displacing a leaving group, such as chloro, bromo, iodo, tosyl and the like, from the heteroaryl or heterocyclic intermediate with the amino group of the amino acid derivative; or by reductive alkylation of the amino group of amino acid derivative with a carbonyl-functionalized intermediate. Such coupling reactions are well-known to those skilled in the art.

By way of illustration, the synthesis of a representative compound of formula Ia is shown in Scheme 1.

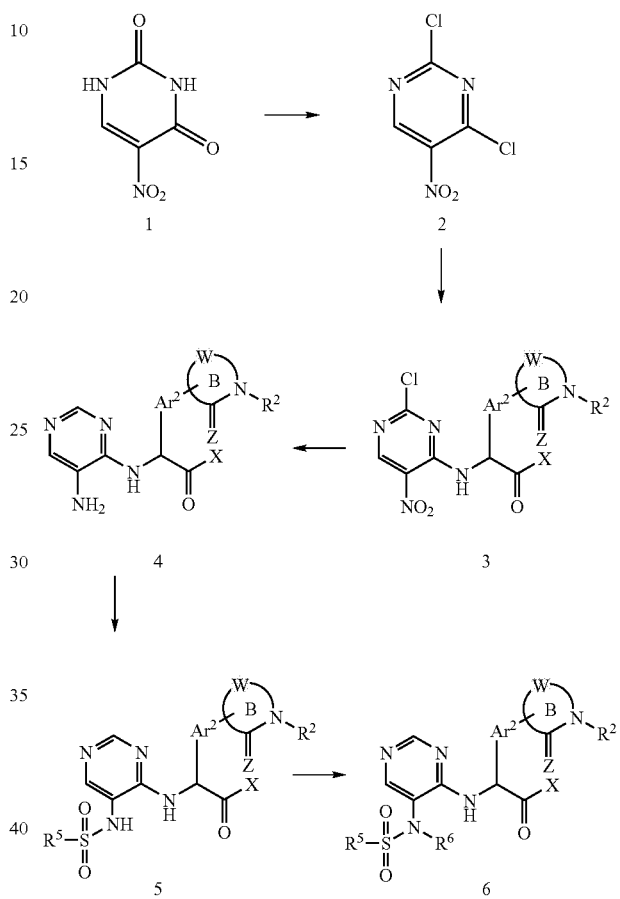

As shown in Scheme 1, 5-nitrouracil, 1, (commercially available from Aldrich Chemical Company, Milwaukee, Wis. USA) is treated with phosphorus oxychloride and N,N-dimethylaniline according to the procedure described in Whittaker, *J. Chem. Soc.* 1951, 1565 to give 1,3-dichloro-4-nitropyrimidine, 2.

1,3-Dichloro-4-nitropyrimidine, 2, is then reacted with about one molar equivalent of an amino acid derivative of the formula (a) or (b) shown above in the presence of a trialkylamine, such as diisopropylethylamine (DIEA). Typically, this reaction is conducted in an inert diluent, such as dichloromethane, at a temperature ranging from about 0° C. to about 10° C. for about 5 min. to about 6 hours to afford intermediate 3 where X is —$OP^1$.

The nitro group of intermediate 3 is then reduced using a conventional reducing agent, such as hydrogen and a palladium on carbon catalyst. When hydrogen and palladium on carbon are employed as the reducing agent, the chloro group of intermediate 3 is also removed. This reaction is typically conducted by contacting 3 with a Degussa-type palladium on carbon catalyst (typically 20%) and excess sodium bicarbonate in an inert diluent, such as methanol, under hydrogen (typically about 55 psi) for about 12 to 36 hours at ambient temperature to afford amino intermediate 4.

Amino intermediate 4 is then reacted with a sulfonyl chloride of the formula: $R^5$—$S(O)_2$—Cl, where $R^5$ is as defined herein, to provide sulfonamide intermediate 5. This reaction is typically conducted by reacting the amino intermediate 4 with at least one equivalent, preferably about 1.1 to about 2 equivalents, of the sulfonyl chloride in an inert diluent such as dichloromethane and the like. Generally, the reaction is conducted at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines such as triethylamine, diisopropylethylamine, N-methylmorpholine and the like. Alternatively, the reaction can be conducted under Schotten-Baumann-type conditions using aqueous alkali, such as sodium hydroxide and the like, as the base. Upon completion of the reaction, the resulting sulfonamide 5 is recovered by conventional methods including neutralization, extraction, precipitation, chromatography, filtration, and the like.

Other heteroaryl intermediates may also be employed in the above described reactions including, but not limited to, 2-chloro-3-nitropyrazine (*J. Med. Chem.* 1984, 27, 1634); 4-chloro-5-nitroimidazole (*J. Chem. Soc.* 1930, 268); and the like.

The amino acid derivatives (a) or (b), employed in the above reactions can be prepared from known amino acids or by known methods for the preparation of amino acids. For example, amino acid derivatives (a) or (b) where $Ar^1$ is aryl, specifically phenyl, can be prepared from commercially available 4'-iodophenylalanine (Aldrich) as follows. 4'-Iodophenylalanine is first converted in two steps to give N-tert-butoxycarbonyl-4'-iodophenylalanine methyl ester (see., *J. Am. Chem. Soc.* 1992, 114(19), 7597-7598). The latter compound is then reacted with a suitably substituted (trialkylstannyl)-heterocycle (see., *J. Org. Chem.* 1994, 59(20), 5905-5911) or a suitably substituted (dihydroxyboronyl) heterocycle (see., *Tet. Lett.* 1993, 34(13), 2127-2130), utilizing a palladium catalyst to form a carbon-carbon bond, to give an N-tert-butoxycarbonyl-4'-(heterocyclyl)-phenylalanine methyl ester. (A detailed description of the synthesis of N-tert-butoxycarbonyl-4-(1-methyl-4-methoxypyridin-2-one-3-yl)-L-phenylalanine methyl ester is provided in working examples.) The latter compound can be reacted with hydrogen-chloride to give the hydrochloride salt of a 4'-(heterocyclyl)phenylalanine methyl ester, which-would be suitable for use in a reaction described above.

Alternatively for example, N-tert-butoxycarbonyl-4'-iodophenylalanine methyl ester can be converted in one step to give either N-tert-butoxycarbonyl-4'-(trimethylstannyl)phenylalanine methyl ester (see., *Syn. Lett.* 1997, (7), 1403-1405) or N-tert-butoxycarbonyl-4'-(pinacolatoboronno)phenylalanine methyl ester (see., *Tet. Lett.* 1999, 40(2), 213-216). Either of the latter compounds could be reacted with a suitably substituted iodoheterocycle or bromoheterocycle, utilizing a palladium catalyst to form a carbon-carbon bond, to give an N-tert-butoxycarbonyl-4'-(heterocyclyl)phenylalanine methyl ester (see., *Syn. Lett.* 1997, (7), 1403-1405; *Tetrahedron Lett.* 1999, 40(2), 213-216). The tert-butoxycarbonyl group of the latter compound could be removed as described above. Alternatively for example, N-tert-butoxycarbonyl-4'-iodophenylalanine methyl ester could be reacted with a suitably substituted heterocycle featuring an N—H group, utilizing a copper catalyst to form a carbon-nitrogen bond, to give an N-tert-butoxycarbonyl-4'-(heterocyclyl)phenylalanine methyl ester (see., *J. Med. Chem.* 1998, 41(13), 2268-2277). The tert-butoxycarbonyl group of the latter compound could be removed as described above. Alternatively, for example, commercially available 4'-nitrophenylalanine (Aldrich) could be converted in three steps to N-tert-butoxycarbonyl-4'-aminophenylalanine methyl ester (see., *J. Org. Chem.* 1999, 64(10), 3467-3475). The latter compound could be reacted with an omega-haloalkyl-isocyanate to give an N-tert-butoxycarbonyl-4'-(omega-haloalkylaminocarbonyl-)amino)-phenylalanine methyl ester (see., *Khim. Farm. Zh.* 1984, 18(12), 1432-1436). The latter compound could be reacted with sodium hydride to give an N-tert-butoxycarbonyl-4'-(1,3-diaza-2-oxoalicyclyl)phenylalanine methyl ester (see., *Bioorg. Med. Chem. Lett.* 1999, 9(5), 749-754). The tert-butoxycarbonyl group of the latter compound could be removed as described above.

For example, amino acid derivatives (a) or (b) where $Ar^1$ is heteroaryl, these can be prepared by methods well known in the art. For example, the procedures of Schow et al. (*J. Org. Chem.* 1994, 59(22), 6850-6852) or the procedures of Ye et al. (*J. Org. Chem.* 1995, 60(8), 2640-2641) or the procedures of Myers et al. (*J. Org. Chem.* 1996, 61(22), 813-815) may be used to prepare 5-hydroxypyridin-2-ylalanine. Using standard procedures, the carboxyl group could be protected with a methyl ester, and the amino group could be protected with tert-butoxycarbonyl group. The procedure of Ksander et al. (*J. Med. Chem.* 1995, 38(10), 1689-1700) could be used to convert the phenol of such a protected derivative into a triflate. The procedure of Firooznia et al. (*Tet. Lett.* 1999, 40(2), 213-216) could be used to convert the triflate into pinacolatoborono derivative. As described above, the pinacolatoborono derivative could be applied in a palladium catalyzed coupling with a suitably substituted iodoheterocycle or bromoheterocycle.

The procedures of Yamano et al. (*Tetrahedron.* 1992, 48(8), 1457-1464) or the procedures of Andrews et al. (*J. Chem. Soc. Perkin Trans.* 1. 1995, 11, 1335-1340) may be used to prepare 2-hydroxypyridin-2-ylalanine. Using procedures described above, this could be converted into a protected pinacolatoborono derivative, which could be applied in a palladium catalyzed coupling with a suitably substituted iodoheterocycle or bromoheterocycle.

The procedures of Shiotani et al. (*J. Org. Chem.* 1997, 34(3), 941-952) could be used to prepare a pyridin-2-one fused via the 4 and 5 positions with a tetrahydrofuran. Following methods described in the working examples, this compound could be elaborated into a 1-methyl-3-iodopyridin-2-one fused via the 4 and 5 positions with a tetrahydrofuran. As described above, this compound could be applied in a palladium catalyzed coupling with a suitably protected pinacolatoborono phenylalanine or a suitably protected pinacolatoborono heteroarylalanine.

The procedures of Adembri (*J. Chem. Soc. Perkin Trans.* 1. 1975. 2190-2194) could be used to prepare a pyridin-2-one fused via the 4 and 5 positions with an isoxazole. Following methods described in the working examples, this compound could be elaborated into a 1-methyl-3-iodopyridin-2-one fused via the 4 and 5 positions with an isoxazole. As described above, this compound could be applied in a palladium catalyzed coupling with a suitably protected pinacolatoborono phenylalanine or a suitably protected pinacolatoborono heteroarylalanine.

The procedures of Dorofeenko et al. (*Khim. Geterotsikl. Soedin.* 1976, 533) could be used to prepare a pyridin-2-one fused via the 4 and 5 positions with a furan. Following methods described in the working examples, this compound could be elaborated into a 1-methyl-3-iodopyridin-2-one fused via the 4 and 5 positions with an isoxazole. As described above, this compound could be applied in a palladium catalyzed coupling with a suitably protected pinacolatoborono phenylalanine or a suitably protected pinacolato heteroarylalanine.

The sulfonyl chlorides employed in the above reaction are also either known compounds or compounds that can be prepared from known compounds by conventional synthetic procedures. Such compounds are typically prepared from the corresponding sulfonic acid, i.e., from compounds of the formula $R^5$—$SO_3H$ where $R^5$ is as defined above, using phosphorous trichloride and phosphorous pentachloride. This reaction is generally conducted by contacting the sulfonic acid with about 2 to 5 molar equivalents of phosphorous trichloride and phosphorous pentachloride either neat or in an inert solvent, such as dichloromethane, at temperature in the range of about 0° C. to about 80° C. for about 1 to about 48 hours to afford the sulfonyl chloride. Alternatively, the sulfonyl chloride can be prepared from the corresponding thiol compound, i.e., from compounds of the formula $R^5$—SH where $R^5$ is as defined herein, by treating the thiol with chlorine ($Cl_2$) and water under conventional reaction conditions.

Examples of sulfonyl chlorides suitable for use in this invention include, but are not limited to, methanesulfonyl chloride, 2-propanesulfonyl chloride, 1-butanesulfonyl chloride, benzenesulfonyl chloride, 1-naphthalenesulfonyl chloride, 2-naphthalenesulfonyl chloride, p-toluenesulfonyl chloride, α-toluenesulfonyl chloride, 4-acetamidobenzenesulfonyl chloride, 4-amidinobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-ditrifluoromethylbenzenesulfonyl chloride, 4-fluorobenzenesulfonyl chloride, 4-methoxybenzenesulfonyl chloride, 2-methoxycarbonylbenzenesulfonyl chloride, 4-methylamidobenzenesulfonyl chloride, 4-nitrobenzenesulfonyl chloride, 4-thioamidobenzenesulfonyl chloride, 4-trifluoromethylbenzenesulfonyl chloride, 4-trifluoromethoxybenzenesulfonyl chloride, 2,4,6-trimethylbenzenesulfonyl chloride, 2-phenylethanesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfonyl chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide or sulfonic acid anhydride may be used in place of the sulfonyl chloride in the above reaction to form the sulfonamide intermediate 5.

If desired, sulfonamide intermediate 5 can be alkylated at the sulfonamide nitrogen atom to provide compound 6. For example, 5 can be contacted with excess diazomethane (generated, for example, using 1-methyl-3-nitro-1-nitrosoguanidine and sodium hydroxide) to afford 6 where $R^6$ is methyl. Other conventional alkylation procedures and reagents may also be employed to prepare various compounds of this invention.

In another preferred embodiment, compounds of this invention (Ia) may be prepared by displacement of a leaving group as shown in Scheme 2:

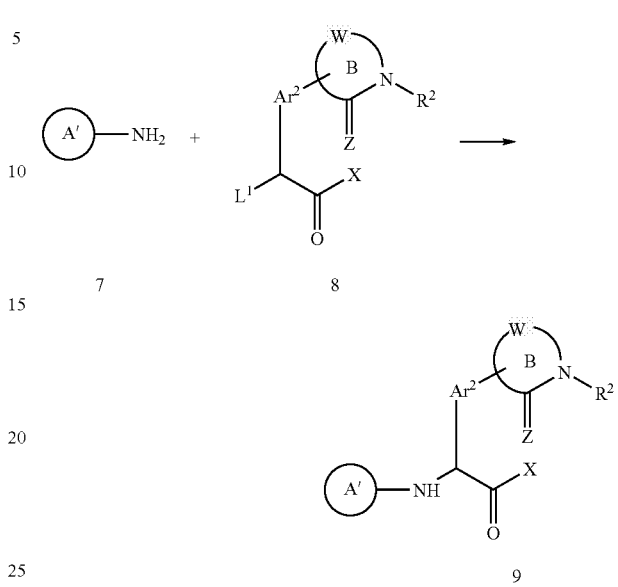

Scheme 2 where B, $Ar^1$, $Ar^2$, and X are as defined herein: A' is heteroaryl, substituted heteroaryl, heterocyclic or substituted heterocyclic containing two nitrogen atoms in the heteroaryl or heterocyclic ring; and $L^1$ is a leaving group, such as chloro, bromo, iodo, sulfonate ester and the like.

Typically, this reaction is conducted by combining approximately stoichiometric equivalents of 7 and 8 in a suitable inert diluent such as water, dimethylsulfoxide (DMSO) and the like, with an excess of a suitable base such as sodium bicarbonate, sodium hydroxide, etc. to scavenge the acid generated by the reaction. The reaction is preferably conducted at from about 25° C. to about 100° C. until reaction completion which typically occurs within 1 to about 24 hours. This reaction is further described in U.S. Pat. No. 3,598,859, which is incorporated herein by reference in its entirety. Upon reaction completion, the product 9 is recovered by conventional methods including precipitation, chromatography, filtration and the like.

In still another alternative embodiment, compounds of this invention can be prepared by reductive amination of a suitable 2-oxocarboxylic acid ester, 10, such as a pyruvate ester, as shown in Scheme 3:

Scheme 3

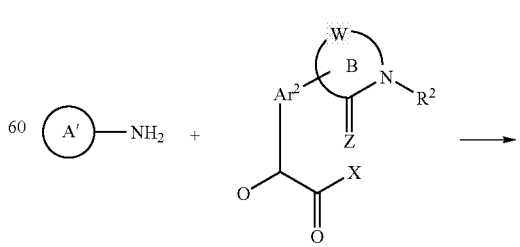

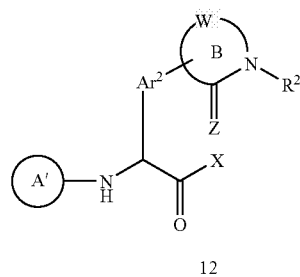

12 where B, Ar¹, Ar², and X are as defined herein.

Generally, this reaction is conducted by combining equamolar amounts of 10 and 11 in an inert diluent such as methanol, ethanol and the like under conditions which provide for imine formation (not shown). The imine formed is then reduced under conventional conditions by a suitable reducing agent such as sodium cyanoborohydride, H₂/palladium on carbon and the like to form the product 12. In a particularly preferred embodiment, the reducing agent is H₂/palladium on carbon which is incorporated into the initial reaction medium thereby permitting imine reduction in situ in a one pot procedure to provide 12. The reaction is preferably conducted at from about 20° C. to about 80° C. at a pressure of from 1 to 10 atmospheres until reaction completion which typically occurs within 1 to about 24 hours. Upon reaction completion, the product 12 is recovered by conventional methods including chromatography, filtration and the like.

Alternatively, certain compounds of this invention can be prepared via a rhodium-catalyzed insertion reaction as shown in Scheme 4:

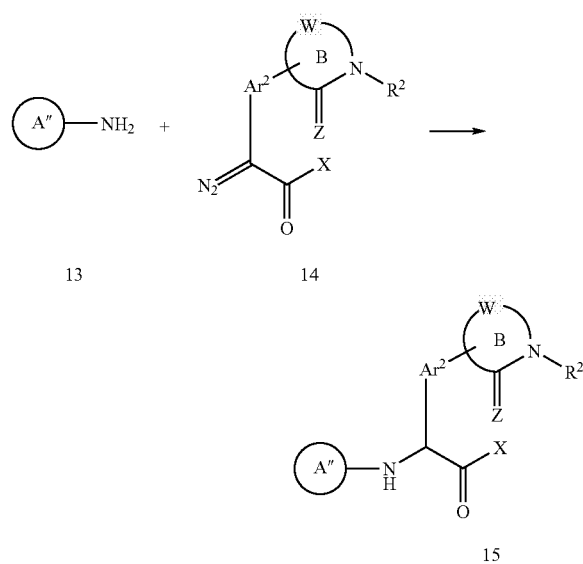

where A" is heteroaryl or substituted heteroaryl containing two nitrogen atoms in the heteroaryl ring, and B, Ar¹, Ar², and X (preferably alkoxy) are as defined herein. Typically, this reaction is conducted using rhodium acetate dimer, Rh₂(OAc)₄, in an inert diluent such as toluene at a temperature ranging from about 25° C. to about 80° C. for about 1 to 12 hours to afford 15. This reaction is described further in B. R. Henke et. al., *J. Med. Chem.* 1998, 41, 5020-5036 and references cited therein.

Similarly, certain compounds of this invention can be prepared by the copper-catalyzed coupling reaction shown in Scheme 5:

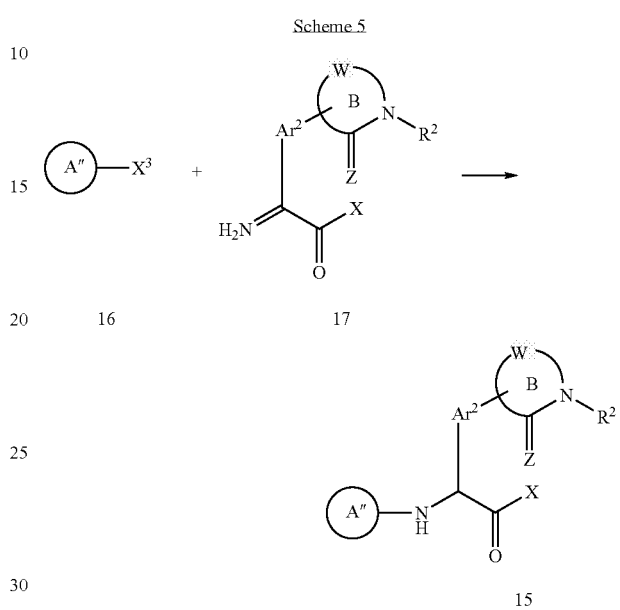

where A" is as defined herein, X³ is halogen, such as chloro, bromo or iodo (preferably iodo) and B, Ar¹, Ar², and X (preferably alkoxy) are as defined herein. Typically, this reaction is conducted using copper iodide (CuI) and potassium carbonate in an inert diluent such as N,N-dimethyl acetamide (DMA) at a temperature ranging from about 60° C. to about 120° C. for about 12 to 36 hours to afford 15. This reaction is described further in D. Ma et. al., *J. Am. Chem. Soc.* 1998, 120, 12459-12467 and references cited therein. It should be recognized by on one skilled in the art that although Applicants have depicted use of amino acid of formula (a) in the above schemes that one could readily use amino acid of formula (b) in the above reactions to get to compound of Formula (Ib).

For ease of synthesis, the compounds of this invention are typically prepared as an ester, i.e., where X is an alkoxy or substituted alkoxy group and the like. If desired, the ester group can be hydrolysed using conventional conditions and reagents to provide the corresponding carboxylic acid. Typically, this reaction is conducted by treating the ester with at least one equivalent of an alkali metal hydroxide, such as lithium, sodium or potassium hydroxide, in an inert diluent, such as methanol or mixtures of methanol and water, at a temperature ranging about 0° C. to about 24° C. for about 1 to about 12 hours. Alternatively, benzyl esters may be removed by hydrogenolysis using a palladium catalyst, such as palladium on carbon, and tert-butyl esters can be removed using formic acid to afford the corresponding carboxylic acid.

As will be apparent to those skilled in the art, other functional groups present on any of the substituents of the compounds of formulas I-II can be readily modified or derivatized either before or after the above-described synthetic reactions using well-known synthetic procedures. For example, a nitro group present on a substituent of a compound of formula I-II or an intermediate thereof may be readily reduced by hydrogenation in the presence of a palladium catalyst, such as palladium on carbon, to provide the corresponding amino group. This reaction is typically conducted at a temperature of from about 20° C. to about 50° C. for about 6 to about 24 hours in an inert diluent, such as methanol. Compounds having a nitro group on the $Ar^2$ substituent can be prepared, for example, by using a 4-nitrophenylalanine derivative and the like in the above-described coupling reactions.

Similarly, a pyridyl group can be hydrogenated in the presence of a platinum catalyst, such as platinum oxide, in an acidic diluent to provide the corresponding piperidinyl analogue. Generally, this reaction is conducted by treating the pyridine compound with hydrogen at a pressure ranging from about 20 psi to about 60 psi, preferably about 40 psi, in the presence of the catalyst at a temperature of about 20° C. to about 50° C. for about 2 to about 24 hours in an acidic diluent, such as a mixture of methanol and aqueous hydrochloric acid.

Additionally, when the $Ar^1$ substituent of a compound of formula I-II contains a primary or secondary amino group, such amino groups can be further derivatized either before or after the above coupling reactions to provide, by way of example, amides, sulfonamides, ureas, thioureas, carbamates, secondary or tertiary amines and the like. Compounds having a primary amino group on the $Ar^1$ substituent may be prepared, for example, by reduction of the corresponding nitro compound as described above.

By way of illustration, a compound of formula I-II or an intermediate thereof having a substituent containing a primary or secondary amino group, can be readily N-acylated using conventional acylating reagents and conditions to provide the corresponding amide. This acylation reaction is typically conducted by treating the amino compound with at least one equivalent, preferably about 1.1 to about 1.2 equivalents, of a carboxylic acid in the presence of a coupling reagent such as a carbodiimide, BOP reagent (benzotriazol-1-yloxy-tris(dimethylamino)phosphonium hexafluorophosphonate) and the like in an inert diluent, such as dichloromethane, chloroform, acetonitrile, tetrahydrofuran, N,N-dimethylformamide and the like, at a temperature ranging from about 0° C. to about 37° C. for about 4 to about 24 hours. Preferably, a promoter, such as N-hydroxysuccinimide, 1-hydroxy-benzotriazole and the like, is used to facilitate the acylation reaction. Examples of carboxylic acids suitable for use in this reaction include, but are not limited to, N-tert-butyloxycarbonylglycine, N-tert-butyloxycarbonyl-L-phenylalanine, N-tert-butyloxycarbonyl-L-aspartic acid benzyl ester, benzoic acid, N-tert-butyloxycarbonylisonipecotic acid, N-methylisonipecotic acid, N-tert-butyloxycarbonylnipecotic acid, N-tert-butyloxycarbonyl-L-tetrahydroisoquinoline-3-carboxylic acid, N-(toluene-4-sulfonyl)-L-proline and the like.

Alternatively, a compound of formula I-II or an intermediate thereof containing a primary or secondary amino group can be N-acylated using an acyl halide or a carboxylic acid anhydride to form the corresponding amide. This reaction is typically conducted by contacting the amino compound with at least one equivalent, preferably about 1.1 to about 1.2 equivalents, of the acyl halide or carboxylic acid anhydride in an inert diluent, such as dichloromethane, at a temperature ranging from about −70° C. to about 40° C. for about 1 to about 24 hours. If desired, an acylation catalyst such as 4-(N,N-dimethylamino)pyridine may be used to promote the acylation reaction. The acylation reaction is preferably conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like.

Examples of acyl halides and carboxylic acid anhydrides suitable for use in this reaction include, but are not limited to, 2-methylpropionyl chloride, trimethylacetyl chloride, phenylacetyl chloride, benzoyl chloride, 2-bromobenzoyl chloride, 2-methylbenzoyl chloride, 2-trifluoro-methylbenzoyl chloride, isonicotinoyl chloride, nicotinoyl chloride, picolinoyl chloride, acetic anhydride, succinic anhydride, and the like. Carbamyl chlorides, such as N,N-dimethylcarbamyl chloride, N,N-diethylcarbamyl chloride and the like, can also be used in this reaction to provide ureas. Similarly, dicarbonates, such as di-tert-butyl dicarbonate, may be employed to provide carbamates.

In a similar manner, a compound of formula I-II or an intermediate thereof containing a primary or secondary amino group may be N-sulfonated to form a sulfonamide using a sulfonyl halide or a sulfonic acid anhydride. Sulfonyl halides and sulfonic acid anhydrides suitable for use in this reaction include, but are not limited to, methanesulfonyl chloride, chloromethanesulfonyl chloride, p-toluenesulfonyl chloride, trifluoromethanesulfonic anhydride, and the like. Similarly, sulfamoyl chlorides, such as dimethylsulfamoyl chloride, can be used to provide sulfamides (e.g., >N—SO₂—N<).

Additionally, a primary and secondary amino group present on a substituent of a compound of formula I-II or an intermediate thereof can be reacted with an isocyanate or a thioisocyanate to give a urea or thiourea, respectively. This reaction is typically conducted by contacting the amino compound with at least one equivalent, preferably about 1.1 to about 1.2 equivalents, of the isocyanate or thioisocyanate in an inert diluent, such as toluene and the like, at a temperature ranging from about 24° C. to about 37° C. for about 12 to about 24 hours. The isocyanates and thioisocyanates used in this reaction are commercially available or can be prepared from commercially available compounds using well-known synthetic procedures. For example, isocyanates and thioisocyanates are readily prepared by reacting the appropriate amine with phosgene or thiophosgene. Examples of isocyanates and thioisocyanates suitable for use in this reaction include, but are not limited to, ethyl isocyanate, n-propyl isocyanate, 4-cyanophenyl isocyanate, 3-methoxyphenyl isocyanate, 2-phenylethyl isocyanate, methyl thioisocyanate, ethyl thioisocyanate, 2-phenylethyl thioisocyanate, 3-phenylpropyl thioisocyanate, 3-(N,N-diethylamino)propyl thioisocyanate, phenyl thioisocyanate, benzyl thioisocyanate, 3-pyridyl thioisocyanate, fluorescein isothiocyanate (isomer I) and the like.

Furthermore, when a compound of formula I-II or an intermediate thereof contains a primary or secondary amino group, the amino group can be reductively alkylated using aldehydes or ketones to form a secondary or tertiary amino group. This reaction is typically conducted by contacting the amino compound with at least one equivalent, preferably about 1.1 to about 1.5 equivalents, of an aldehyde or ketone and at least one equivalent based on the amino compound of a metal hydride reducing agent, such as sodium cyanoborohydride, in an inert diluent, such as methanol, tetrahydrofuran, mixtures thereof and the like, at a temperature ranging from about 0° C. to about 50° C. for about 1 to about 72 hours. Aldehydes and ketones suitable for use in this reaction include, by way of example, benzaldehyde, 4-chlorobenzaldehyde, valeraldehyde and the like.

In a similar manner, when a compound of formula I-II or an intermediate thereof has a substituent containing a hydroxyl group, the hydroxyl group can be further modified or derivatized either before or after the above coupling reactions to provide, by way of example, ethers, carbamates and the like.

By way of example, a compound of formula I-II or an intermediate thereof having a substituent containing a hydroxyl group, such as where the lactam ring is 4-hydroxypyridone group, can be readily O-alkylated to form ethers. This O-alkylation reaction is typically conducted by contacting the hydroxy compound with a suitable alkali or alkaline earth metal base, such as potassium carbonate, in an inert diluent, such as acetone, 2-butanone and the like, to form the alkali or alkaline earth metal salt of the hydroxyl group. This salt is generally not isolated, but is reacted in situ with at least one equivalent of an alkyl or substituted alkyl halide or sulfonate, such as an alkyl chloride, bromide, iodide, mesylate or tosylate, to afford the ether. Generally, this reaction is conducted at a temperature ranging from about 60° C. to about 150° C. for about 24 to about 72 hours. Preferably, a catalytic amount of sodium or potassium iodide is added to the reaction mixture when an alkyl chloride or bromide is employed in the reaction.

Examples of alkyl or substituted alkyl halides and sulfonates suitable for use in this reaction include, but are not limited to, tert-butyl bromoacetate, N-tert-butyl chloroacetamide, 1-bromoethylbenzene, ethyl α-bromophenylacetate, 2-(N-ethyl-N-phenylamino)ethyl chloride, 2-(N,N-ethylamino)ethyl chloride, 2-(N,N-diisopropylamino)ethyl chloride, 2-(N,N-dibenzylamino)ethyl chloride, 3-(N,N-ethylamino)propyl chloride, 3-(N-benzyl-N-methylamino)propyl chloride, N-(2-chloroethyl)morpholine, 2-(hexamethyleneimino)ethyl chloride, 3-(N-methylpiperazine)propyl chloride, 1-(3-chlorophenyl)-4-(3-chloropropyl)piperazine, 2-(4-hydroxy-4-phenylpiperidine)ethyl chloride, N-tert-butyloxycarbonyl-3-piperidinemethyl tosylate, and the like.

Alternatively, a hydroxyl group present on a substituent of a compound of formula I-II or an intermediate thereof can be O-alkylating using the Mitsunobu reaction. In this reaction, an alcohol, such as 3-(N,N-dimethylamino)-1-propanol and the like, is reacted with about 1.0 to about 1.3 equivalents of triphenylphosphine and about 1.0 to about 1.3 equivalents of diethyl azodicarboxylate in an inert diluent, such as tetrahydrofuran, at a temperature ranging from about −10° C. to about 5° C. for about 0.25 to about 1 hour. About 1.0 to about 1.3 equivalents of a hydroxy compound, such as N-tert-butyltyrosine methyl ester, is then added and the reaction mixture is stirred at a temperature of about 0° C. to about 30° C. for about 2 to about 48 hours to provide the O-alkylated product.

In a similar manner, a compound of formula I-II or an intermediate thereof containing an aryl hydroxy group can be reacted with an aryl iodide to provide a diaryl ether. Generally, this reaction is conducted by forming the alkali metal salt of the hydroxyl group using a suitable base, such as sodium hydride, in an inert diluent such as xylenes at a temperature of about −25° C. to about 10° C. The salt is then treated with about 1.1 to about 1.5 equivalents of cuprous bromide dimethyl sulfide complex at a temperature ranging from about 10° C. to about 30° C. for about 0.5 to about 2.0 hours, followed by about 1.1 to about 1.5 equivalents of an aryl iodide, such as sodium 2-iodobenzoate and the like. The reaction is then heated to about 70° C. to about 150° C. for about 2 to about 24 hours to provide the diaryl ether.

Additionally, a hydroxy-containing compound can also be readily derivatized to form a carbamate. In one method for preparing such carbamates, a hydroxy compound of formula I-II or an intermediate thereof is contacted with about 1.0 to about 1.2 equivalents of 4-nitrophenyl chloroformate in an inert diluent, such as dichloromethane, at a temperature ranging from about −25° C. to about 0° C. for about 0.5 to about 2.0 hours. Treatment of the resulting carbonate with an excess, preferably about 2 to about 5 equivalents, of a trialkylamine, such as triethylamine, for about 0.5 to 2 hours, followed by about 1.0 to about 1.5 equivalents of a primary or secondary amine provides the carbamate. Examples of amines suitable for using in this reaction include, but are not limited to, piperazine, 1-methylpiperazine, 1-acetylpiperazine, morpholine, thiomorpholine, pyrrolidine, piperidine and the like.

Alternatively, in another method for preparing carbamates, a hydroxy-containing compound is contacted with about 1.0 to about 1.5 equivalents of a carbamyl chloride in an inert diluent, such as dichloromethane, at a temperature ranging from about 25° C. to about 70° C. for about 2 to about 72 hours. Typically, this reaction is conducted in the presence of a suitable base to scavenge the acid generated during the reaction. Suitable bases include, by way of example, tertiary amines, such as triethylamine, diisopropylethylamine, N-methylmorpholine and the like. Additionally, at least one equivalent (based on the hydroxy compound) of 4-(N,N-dimethylamino)pyridine is preferably added to the reaction mixture to facilitate the reaction. Examples of carbamyl chlorides suitable for use in this reaction include, by way of example, dimethylcarbamyl chloride, diethylcarbamyl chloride and the like.

Likewise, when a compound of formula I-II or an intermediate thereof contains a primary or secondary hydroxyl group, such hydroxyl groups can be readily converted into a leaving group and displaced to form, for example, amines, sulfides and fluorides. Generally, when a chiral compound is employed in these reactions, the stereochemistry at the carbon atom attached to the derivatized hydroxyl group is typically inverted.

These reactions are typically conducted by first converting the hydroxyl group into a leaving group, such as a tosylate, by treatment of the hydroxy compound with at least one equivalent of a sulfonyl halide, such as p-toluenesulfonyl chloride and the like, in pyridine. This reaction is generally conducted at a temperature of from about 0° C. to about 70° C. for about 1 to about 48 hours. The resulting tosylate can then be readily displaced with sodium azide, for example, by contacting the tosylate with at least one equivalent of sodium azide in an inert diluent, such as a mixture of N,N-dimethylformamide and water, at a temperature ranging from about 0° C. to about 37° C. for about 1 to about 12 hours to provide the corresponding azido compound. The azido group can then be reduced by, for example, hydrogenation using a palladium on carbon catalyst to provide the amino ($-NH_2$) compound.

Similarly, a tosylate group can be readily displaced by a thiol to form a sulfide. This reaction is typically conducted by contacting the tosylate with at least one equivalent of a thiol, such as thiophenol, in the presence of a suitable base, such as 1,8-diazabicyclo[5.4.0]undec-7-ene (DBU), in an inert diluent, such as N,N-dimethylformamide, at a temperature of from about 0° C. to about 37° C. for about 1 to about 12 hours to provide the sulfide. Additionally, treatment of a tosylate with morpholinosulfur trifluoride in an inert diluent, such as dichloromethane, at a temperature ranging from about 0° C. to about 37° C. for about 12 to about 24 hours affords the corresponding fluoro compound.

Furthermore, a compound of formula I-II or an intermediate thereof having a substituent containing an iodoaryl group can be readily converted either before or after the above coupling reactions into a biaryl compound. Typically, this reaction is conducted by treating the iodoaryl compound with about 1.1 to about 2 equivalents of an arylzinc iodide, such as 2-(methoxycarbonyl)phenylzinc iodide, in the presence of a palladium catalyst, such as palladium tetra(triphenylphosphine), in an inert diluent, such as tetrahydrofuran, at a temperature ranging from about 24° C. to about 30° C. until reaction completion. This reaction is further described, for example, in Rieke, *J. Org. Chem.* 1991, 56, 1445. Additional methods for preparing biaryl derivatives are disclosed in International Publication Number WO 98/53817, published Dec. 3, 1998, the disclosure of which is incorporated herein by reference in its entirety.

In some cases, the compounds of formula I-II or intermediates thereof may contain substituents having one or more sulfur atoms. When present, such sulfur atoms can be oxidized either before or after the above coupling reactions to provide a sulfoxide or sulfone compound using conventional reagents and reaction conditions. Suitable reagents for oxidizing a sulfide compound to a sulfoxide include, by way of example, hydrogen peroxide, 3-chloroperoxybenzoic acid (MCPBA), sodium periodate and the like. The oxidation reaction is typically conducted by contacting the sulfide compound with about 0.95 to about 1.1 equivalents of the oxidizing reagent in an inert diluent, such as dichloromethane, at a temperature ranging from about −50° C. to about 75° C. for about 1 to about 24 hours. The resulting sulfoxide can then be further oxidized to the corresponding sulfone by contacting the sulfoxide with at least one additional equivalent of an oxidizing reagent, such as hydrogen peroxide, MCPBA, potassium permanganate and the like. Alternatively, the sulfone can be prepared directly by contacting the sulfide with at least two equivalents, and preferably an excess, of the oxidizing reagent. Such reactions are described further in March, *"Advanced Organic Chemistry"*, 4th Ed., pp. 1201-1202, Wiley Publisher, 1992.

Other procedures and reaction conditions for preparing the compounds of this invention are described in the examples set forth below. Additionally, other procedures for preparing compounds useful in certain aspects of this invention are disclosed in U.S. applications Ser. Nos. 09/489,377 and 09/489,378, filed on Jan. 21, 2000, entitled "Compounds Which Inhibit Leucocyte Adhesion Mediated by VLA-4"; the disclosure of which is incorporated herein by reference in its entirety.

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I-VII above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) | 50.0 mg |
| Microcrystalline cellulose (89%) | |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

Formulation Example 9

An intravenous formulation may be prepared as follows:

| Ingredient | Quantity |
| --- | --- |
| Active Ingredient | 250.0 mg |
| Isotonic saline | 1000 ml |

Formulation Example 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Utility

The compounds of this invention can be employed to bind VLA-4 ($\alpha_4\beta_1$ integrin) in biological samples, i.e., the compounds bind VLA-4 with an $IC_{50}$ of 15 μM or less in a competitive binding assay as described herein. Accordingly, these compounds have utility in, for example, assaying such samples for VLA-4. In such assays, the compounds can be bound to a solid support and the VLA-4 sample added thereto. The amount of VLA-4 in the sample can be determined by conventional methods such as use of a sandwich ELISA assay. Alternatively, labeled VLA-4 can be used in a competitive assay to measure for the presence of VLA-4 in the sample. Other suitable assays are well known in the art.

In addition, certain of the compounds of this invention inhibit, in vivo, adhesion of leukocytes to endothelial cells mediated by VLA-4 by competitive binding to VLA-4. Accordingly, the compounds of this invention can be used in the treatment of diseases mediated by VLA-4 or leucocyte adhesion. Such diseases include inflammatory diseases in mammalian patients such as asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

The biological activity of the compounds identified above may be assayed in a variety of systems. For example, a compound can be immobilized on a solid surface and adhesion of cells expressing VLA-4 can be measured. Using such formats, large numbers of compounds can be screened. Cells suitable for this assay include any leukocytes known to express VLA-4 such as T cells, B cells, monocytes, eosinophils, and basophils. A number of leukocyte cell lines can also be used, examples include Jurkat and U937.

The test compounds can also be tested for the ability to competitively inhibit binding between VLA-4 and VCAM-1, or between VLA-4 and a labeled compound known to bind VLA-4 such as a compound of this invention or antibodies to VLA-4. In these assays, the VCAM-1 can be immobilized on a solid surface. VCAM-1 may also be expressed as a recombinant fusion protein having an Ig tail (e.g., IgG) so that binding to VLA-4 may be detected in an immunoassay. Alternatively, VCAM-1 expressing cells, such as activated endothelial cells or VCAM-1 transfected fibroblasts can be used. For assays to measure the ability to block adhesion to brain endothelial cells, the assays described in International Patent Application Publication No. WO 91/05038 are particularly preferred. This application is incorporated herein by reference in its entirety.

Many assay formats employ labelled assay components. The labelling systems can be in a variety of forms. The label may be coupled directly or indirectly to the desired component of the assay according to methods well known in the art. A wide variety of labels may be used. The component may be labelled by any one of several methods. The most common method of detection is the use of autoradiography with $^3$H, $^{125}$I, $^{35}$S, $^{14}$C, or $^{37}$P labelled compounds or the like. Non-radioactive labels include ligands which bind to labelled antibodies, fluorophores, chemiluminescent agents, enzymes and antibodies which can serve as specific binding pair members for a labelled ligand. The choice of label depends on sensitivity required, ease of conjugation with the compound, stability requirements, and available instrumentation.

Appropriate in vivo models for demonstrating efficacy in treating inflammatory responses include EAE (experimental autoimmune encephalomyelitis) in mice, rats, guinea pigs or primates, as well as other inflammatory models dependent upon α4 integrins.

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the proteins during incubation with peptidases or human plasma or serum. A number of such protein stability assays have been described (see, e.g., Verhoef et al., Eur. J. Drug Metab. Pharmacokinet., 1990, 15(2):83-93).

For diagnostic purposes, a wide variety of labels may be linked to the compounds, which may provide, directly or indirectly, a detectable signal. Thus, the compounds of the subject invention may be modified in a variety of ways for a variety of end purposes while still retaining biological activity. In addition, various reactive sites may be introduced at the terminus for linking to particles, solid substrates, macromolecules, or the like.

Labeled compounds can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

In vitro uses include diagnostic applications such as monitoring inflammatory responses by detecting the presence of leukocytes expressing VLA-4. The compounds of this invention can also be used for isolating or labeling such cells. In addition, as mentioned above, the compounds of the invention can be used to assay for potential inhibitors of VLA-4/VCAM-1 interactions.

For in vivo diagnostic imaging to identify, e.g., sites of inflammation, radioisotopes are typically used in accordance with well known techniques. The radioisotopes may be bound to the peptide either directly or indirectly using intermediate functional groups. For instance, chelating agents such as diethylenetriaminepentacetic acid (DTPA) and ethylenediaminetetraacetic acid (EDTA) and similar molecules have been used to bind proteins to metallic ion radioisotopes.

The complexes can also be labeled with a paramagnetic isotope for purposes of in vivo diagnosis, as in magnetic resonance imaging (MRI) or electron spin resonance (ESR), both of which are well known. In general, any conventional method for visualizing diagnostic imaging can be used. Usually gamma- and positron-emitting radioisotopes are used for camera imaging and paramagnetic isotopes are used for MRI. Thus, the compounds can be used to monitor the course of amelioration of an inflammatory response in an individual. By measuring the increase or decrease in lymphocytes expressing VLA-4 it is possible to determine whether a particular therapeutic regimen aimed at ameliorating the disease is effective.

The pharmaceutical compositions of the present invention can be used to block or inhibit cellular adhesion associated with a number of diseases and disorders. For instance, a number of inflammatory disorders are associated with integrins or leukocytes. Treatable disorders include, e.g., transplantation rejection (e.g., allograft rejection), Alzheimer's disease, atherosclerosis, AIDS dementia, diabetes (including acute juvenile onset diabetes), retinitis, cancer metastases, rheumatoid arthritis, acute leukocyte-mediated lung injury (e.g., adult respiratory distress syndrome), asthma, nephritis, and acute and chronic inflammation, including atopic dermatitis, psoriasis myocardial ischemia, and inflammatory bowel disease (including Crohn's disease and ulcerative colitis). In preferred embodiments the pharmaceutical compositions are used to treat inflammatory brain disorders, such as multiple sclerosis (MS), viral meningitis and encephalitis.

Inflammatory bowel disease is a collective term for two similar diseases referred to as Crohn's disease and Ulcerative colitis. Crohn's disease is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, *Immunology* (3d ed., Raven Press, 1993).

Another indication for the compounds of this invention is in treatment of organ or graft rejection mediated by VLA-4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. CD8+ cells, CD4 cells and monocytes are all involved in the rejection of transplant tissues. Compounds of this invention which bind to alpha-4 integrin are useful, inter alia, to block alloantigen-induced immune responses in the donee thereby preventing such cells from participating in the destruction of the transplanted tissue or organ. See, e.g., Paul et al., *Transplant International* 9, 420-425 (1996); Georczynski et al., *Immunology* 87, 573-580 (1996); Georcyznski et al., *Transplant. Immunol.* 3, 55-61 (1995); Yang et al., *Transplantation* 60, 71-76 (1995); Anderson et al., *APMIS* 102, 23-27 (1994).

A related use for compounds of this invention which bind to VLA-4 is in modulating the immune response involved in "graft versus host" disease (GVHD). See e.g., Schlegel et al., *J. Immunol.* 155, 3856-3865 (1995). GVHD is a potentially fatal disease that occurs when immunologically competent cells are transferred to an allogeneic recipient. In this situation, the donor's inmmunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

A further use of the compounds of this invention is inhibiting tumor metastasis. Several tumor cells have been reported to express VLA-4 and compounds which bind VLA-4 block adhesion of such cells to endothelial cells. Steinback et al., *Urol. Res.* 23, 175-83 (1995); Orosz et al., *Int. J. Cancer* 60, 867-71 (1995); Freedman et al., *Leuk. Lymphoma* 13, 47-52 (1994); Okahara et al., *Cancer Res.* 54, 3233-6 (1994).

A further use of the compounds of this invention is in treating multiple sclerosis. Multiple sclerosis is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against VLA-4 have been shown to block the adhesion of leukocytes to the endothelium, and thus prevent inflammation of the central nervous system and subsequent paralysis in the animals[16].

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985).

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 µg to about 500 µg per kilogram body weight, preferably about 100 µg to about 300 µg per kilogram body weight; Suitable dosage ranges for intranasal administration are generally about 0.1 pg to 1 mg per kilogram body weight. Effective doses can be extrapolated from dose-response curves derived from in vitro or animal model test systems.

Compounds of this invention are also capable of binding or antagonizing the actions of $\alpha_6\beta_1$, $\alpha_9\beta_1$, $\alpha_4\beta_7$, $\alpha_d\beta_2$, $\alpha_e\beta_7$ integrins (although $\alpha_4\beta_1$ and $\alpha_9\beta_1$ are preferred in this invention). Accordingly, compounds of this invention are also useful for preventing or reversing the symptoms, disorders or diseases induced by the binding of these integrins to their respective ligands.

For example, International Publication Number WO 98/53817, published Dec. 3, 1998 (the disclosure of which is incorporated herein by reference in its entirety) and references cited therein describe disorders mediated by $\alpha_4\beta_7$. This reference also describes an assay for determining antagonism of $\alpha_4\beta_7$ dependent binding to VCAM-Ig fusion protein.

Additionally, compounds that bind $\alpha_d\beta_2$ and $\alpha_e\beta_7$ integrins are particularly useful for the treatment of asthma and related lung diseases. See, for example, M. H. Grayson et al., *J. Exp. Med.* 1998, 188(11) 2187-2191. Compounds that bind $\alpha_e\beta_7$ integrin are also useful for the treatment of systemic lupus erythematosus (see, for example, M. Pang et al., *Arthritis Rheum.* 1998, 41(8), 1456-1463); Crohn's disease, ulcerative colitis and inflammatory bowel disease (IBD) (see, for example, D. Elewaut et al., *Scand J. Gastroenterol* 1998, 33(7) 743-748); Sjogren's syndrome (see, for example, U. Kroneld et al. *Scand J. Gastroenterol* 1998, 27(3), 215-218); and rheumatoid arthritis (see, for example, *Scand J. Gastroenterol* 1996, 44(3), 293-298). And compounds that bind $\alpha_6\beta_1$ may be useful in preventing fertilization (see, for example, H. Chen et al., *Chem. Biol.* 1999, 6, 1-10).

Certain of the compounds within the generic formulas described herein are also useful as synthetic intermediates for other compounds of this invention as illustrated in the examples herein.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

aq or aq.=aqueous
AcOH=acetic acid
bd=broad doublet
bm=broad multiplet
bs=broad Ringlet
Bn=benzyl
Boc=N-tert-butoxylcarbonyl
Boc$_2$O=di-tert-butyl dicarbonate
BOP=benzotriazol-1-yloxy-tris(dimethylamino)phosphonium hexafluorophosphate
Cbz=carbobenzyloxy
CHCl$_3$=chloroform
CH$_2$Cl$_2$=dichloromethane
(COCl)$_2$=oxalyl chloride
d=doublet
dd=doublet of doublets
dt=doublet of triplets
DBU=1,8-diazabicyclo[5.4.0]undec-7-ene
DCC=1,3-dicyclohexylcarbodiimide
DMAP=4-N,N-dimethylaminopyridine
DME=ethylene-glycol dimethyl ether
DMF=N,N-dimethylformamide
DMSO=dimethylsulfoxide
EDC=1-(3-dimethylaminopropyl)-3-ethylcarbodiimide hydrochloride
Et$_3$N=triethylamine
Et$_2$O=diethyl ether
EtOAc=ethyl acetate
EtOH=ethanol
eq or eq.=equivalent
Fmoc=N-(9-fluorenylmethoxycarbonyl)
FmocONSu=N-(9-fluorenylmethoxycarbonyl)-succinimide
g=grams
h=hour
H$_2$O=water
HBr=hydrobromic acid
HCl=hydrochloric acid
HOBT=1-hydroxybenzotriazole hydrate
hr=hour
K$_2$CO$_3$=potassium carbonate
L=liter
m=multiplet
MeOH=methanol
mg=milligram
MgSO$_4$=magnesium sulfate
mL=milliliter
mm=millimeter
mM=millimolar
mmol=millimol
mp=melting point
N=normal
NaCl=sodium chloride
Na$_2$CO$_3$=sodium carbonate
NaHCO$_3$=sodium bicarbonate
NaOEt=sodium ethoxide
NaOH=sodium hydroxide
NH$_4$Cl=ammonium chloride
NMM=N-methylmorpholine
Phe=L-phenylalanine
Pro=L-proline
psi=pounds per square inch
PtO$_2$=platinum oxide
q=quartet
quint.=quintet
rt=room temperature
s=singlet
sat=saturated
t=triplet
t-BuOH=tert-butanol
TFA=trifluoroacetic acid
THF=tetrahydrofuran
TLC or tlc=thin layer chromatography
Ts=tosyl
TsCl=tosyl chloride
TsOH=tosylate
µL=microliter The following Methods may be used to prepare the compounds of this invention.

Method A 2,4-Dihydroxy-3-iodopyridine Preparation Procedure

A mixture of 2,4-dihydroxypyridine (1.0 eq), $K_2CO_3$ (1.0 eq), and water was stirred at 100° C. so that it became homogeneous. With continued stirring and heating, $I_2$ (1.0 eq) was added in portions, causing the evolution of gas. When the solid $I_2$ was consumed, the mixture was cooled and acidified with aqueous $KHSO_4$ (1.0 eq), generating a precipitate. The precipitate was collected by filtration, rinsed with water, and stored under high vacuum, to give 2,4-dihydroxy-3-iodopyridine.

Method B

1-Methyl-3-iodo-4-methoxypyridin-2-one Preparation Procedure

A mixture of 2,4-dihydroxy-3-iodopyridine (1.0 eq), $Cs_2CO_3$ (2.0 eq), MeI (10.0 eq) and anhydrous DMF was stirred at 40° C. for 72 h, and then the DMF and remaining MeI were evaporated. The residue was treated with aqueous $NaS_2O_3$, and the mixture was extracted five times with $CH_2Cl_2$. The $CH_2Cl_2$ extracts were treated with $MgSO_4$, filtered, and evaporated. The residue was recrystallized from hexanes/$CH_2Cl_2$ to give 1-methyl-3-iodo-4-methoxypyridin-2-one.

Method C

N-tert-Butoxycarbonyl-4-(1-methyl-4-methoxypyridin-2-one-3-yl)-L-phenylalanine Methyl Ester Preparation Procedure The procedure of Morera and Ortar (*Syn. Lett.* 1997, (7), 1403-1405) was used to convert 1-methyl-3-iodo-4-methoxypyridin-2-one into N-tert-butoxycarbonyl-4-(1-methyl-4-methoxypyridin-2-one-3-yl)-L-phenylalanine methyl ester.

Method D

BOC Removal Procedure

Anhydrous hydrochloride (HCl) gas was bubbled through a methanolic solution of the appropriate Boc-amino acid ester at 0° C. for 15 minutes and the reaction mixture was stirred for three hours. The solution was concentrated to a syrup and dissolved in $Et_2O$ and reconcentrated. This procedure was repeated and the resulting solid was placed under high vacuum overnight.

Method E

Preparation of Dimethyl 2-Alkylmalonate

To a suspension of sodium hydride 60% dispersion in mineral oil (1.1 eq) in anhydrous THF was added slowly with stirring dimethyl malonate (1.1 eq), causing the evolution of gas. To the resulting solution was added a bromoalkane, iodoalkane, or trifluoromethanesulfonyloxyalkane (1.0 eq), and the mixture was heated to 50° C. for 48 h, at which point TLC indicated consumption of the bromoalkane, iodoalkane, or trifluoromethanesulfonyloxyalkane. The mixture was diluted with diethyl ether and washed with 70% saturated sodium chloride. The organic extracts were treated with anhydrous magnesium sulfate, filtered, and evaporated to afford a dimethyl 2-alkylmalonate of sufficient purity for immediate conversion to a 5-alkyl-4,6-dihydroxypyridine.

Method F

Preparation of 5-Alkyl-4,6-dihydroxypyridine

To a diethyl 2-alkylmalonate or a dimethyl 2-alkylmalonate (1.0 eq) was added formamidine acetate (1.0 eq) and 25% sodium methoxide in methanol (3.3 eq). The resulting slurry was stirred vigorously and heated to 60° C. for 4 h, and then allowed to cool. The slurry was diluted with water, and acidified to pH=2 by addition of HCl. The resulting precipitate was collected by filtration, washed with water, and dried under vacuum, to afford a 5-alkyl-4,6-dihydroxypyrimidine of sufficient purity for immediate conversion to a 5-alkyl-4,6-dichloropyrimidine.

Method G

Preparation of 5-Alkyl-4,6-dichloropyrimidine or 5-Alkoxy-4-chloropyrimidine

To a 5-alkyl-4,6-dihydroxypyrimidine or a 5-alkoxy-4-hydroxypyrimidine (1.0 eq) were added phosphorus oxychloride (15.0 eq) and N,N-dimethylaniline (1.0 eq), and the mixture was heated to 100° C. for 3 h, and then allowed to cool. The resulting solution was poured onto ice, and the mixture was extracted with dichloromethane. The organic extracts were treated with anhydrous magnesium sulfate, filtered, and evaporated to afford a 5-alkyl-4,6-dichloropyrimidine or a 5-alkoxy-4-chloropyrimidine of sufficient purity for immediate conversion to a 5-alkyl-4-N-alkylamino-6-chloropyrimidine or a 5-alkoxy-4-N-alkylaminopyrimidine.

Method H

Preparation of 5-Alkyl-4-N-alkylamino-6-chloropyrimidine or 5-Alkoxy-4-N-alkylaminopyrimidine To a solution of a 5-alkyl-4,6-dichloropyrimidine or a 5-alkoxy-4-chloropyrimidine (1.0 eq) in ethanol were added an alkyl amine (1.2 eq, typically L-4-(N,N-dimethylcarbamyloxy)-phenylalanine tert-butyl ester) and diisopropylethylamine (2.0 eq). The mixture was sealed in a pressure tube and heated to 120° C. for 48 h, at which point TLC indicated consumption of the 5-alkyl-4,6-dichloropyrimidine or the 5-alkoxy-4-chloropyrimidine. The mixture was evaporated, and the residue was partitioned between ethyl acetate and pH=4.5 citrate buffer. The organic extracts were washed with saturated sodium chloride, treated with anhydrous magnesium sulfate, filtered, and evaporated. The residue was purified by chromatography on silica gel using ethyl acetate and hexanes to afford a pure 5-alkyl-4-N-alkylamino-6-chloropyrimidine or 5-alkoxy-4-N-alkylaminopyrimidine.

Method I

Preparation of 5-Alkyl-4-N-alkylaminopyrimidine (Procedure I)

A suspension of 5-alkyl-4-N-alkylamino-6-chloropyrimidine (1.0 eq), and an equal mass 10% palladium on carbon, and sodium bicarbonate (5.0 eq) in methanol was shaken under 55 psi hydrogen gas for 16 h, at which point TLC indicated consumption of the 5-alkyl-4-N-alkylamino-6-chloropyrimidine. The mixture was filtered through Celite and evaporated to give a residue, which was partitioned between ethyl acetate and 70% saturated sodium chloride. The organic extracts were treated with anhydrous magnesium sulfate, filtered, and evaporated. The residue was purified by chromatography on silica gel using ethyl acetate and hexanes to afford a pure 5-alkyl-4-N-alkylaminopyrimidine.

Method J

Preparation of 5-Alkyl-4-N-alkylaminopyrimidine (Procedure II)

A suspension of 5-alkyl-4-N-alkylamino-6-chloropyrimidine (1.0 eq), sodium acetate (10.0 eq), and zinc powder (20.0 eq) in a 9:1 mixture of acetic acid and water was stirred vigorously at 40° C. for 72 h, at which point TLC indicated partial consumption of the 5-alkyl-4-N-alkylamino-6-chloropyrimidine. The supernatant solution was decanted from remaining zinc and evaporated. The residue was partitioned between ethyl acetate and saturated sodium bicarbonate, and the organic extracts were treated with anhydrous magnesium sulfate, filtered, and evaporated. The residue was purified by chromatography on silica gel using ethyl acetate and hexanes to afford a pure 5-alkyl-4-N-alkylaminopyrimidine.

Method K

Ester Hydrolysis Procedure II

To a chilled (0° C.) THF/H$_2$O solution (2:1, 5-10 mL) of the appropriate ester was added LiOH (1.1 equivalents). The temperature was maintained at 0° C. and the reaction was complete in 1-3 hours. The reaction mixture was concentrated and the residue was taken up into H$_2$O and the pH adjusted to 2-3 with aqueous HCl. The product was extracted with ethyl acetate and the combined organic phase was washed with brine, dried over MgSO$_4$, filtered and concentrated to yield the desired acid.

Method L

Preparation of 5-Iodo-4(3H)-pyrimidinone

The procedure of Sakamoto et. al. (Chem. Pharm. Bull. 1986, 34(7), 2719-2724) was used to convert 4(3H)-pyrimidinone into 5-iodo-4(3H)-pyrimidinone.

Example 1

Synthesis of N-(5-(2,2,2-trifluoroethyl)pyrimidin-4-yl)-L-4'-(1-methyl-4-methoxy-2-pyridon-3-yl)phenylalanine 2,4-Dihydroxypyridine was converted via sequential application of methods A, B and C to give N-tert-butoxycarbonyl-4-(1-methyl-4-methoxypyridin-2-one-3-yl)-L-phenylalanine methyl ester. This compound was converted via method D to give 4-(1-methyl-4-methoxypyridin-2-one-3-yl)-L-phenylalaninemethyl ester hydrochloride. 2,2,2-Trifluoroethyltriflate (prepared according to Gassman, et al. J. Org. Chem. 1984, 49(12), 2258-2273) was converted via sequential application of methods E, F and G to give 4,6-dichloro-5-(2,2,2-trifluoroethyl)pyrimidine.

4-(1-Methyl-4-methoxypyridin-2-one-3-yl)-L-phenylalanine methyl ester hydrochloride and 4,6-dichloro-5-(2,2,2-trifluoroethyl)pyrimidine were coupled via method H, and the product transformed via sequential application of methods I and K to give the title compound.

Physical Data were as Follows:

$^1$H NMR (CD$_3$OD): δ=8.4 (s), 8.06 (s), 7.66 (d), 7.25-7.18 (m), 6.45 (d), 5.12-5.08 (m), 3.94-3.9 (m), 3.77 (m), 3.49 (s), 3.35-3.17 (m).

$^{13}$C NMR (CD$_3$OD): δ=173.7, 164.7, 163.2, 160.0, 155.8, 153.4, 138.7, 135.9, 131.9, 131.2, 130.3, 128.0, 113.7, 95.7, 55.2, 55.1, 36.5, 36.2, 31.1, 30.7.

Biological Examples

Example A

In Vitro Assay For Determining Binding of Candidate Compounds to VLA-4

An in vitro assay was used to assess binding of candidate compounds to $\alpha_4\beta_1$ integrin. Compounds which bind in this assay can be used to assess VCAM-1 levels in biological samples by conventional assays (e.g., competitive assays). This assay is sensitive to IC$_{50}$ values as low as about 1 nM.

The activity of $\alpha_4\beta_1$ integrin was measured by the interaction of soluble VCAM-1 with Jurkat cells (e.g., American Type Culture Collection Nos. TIB 152, TIB 153, and CRL 8163), a human T-cell line which expresses high levels of $\alpha_4\beta_1$ integrin. VCAM-1 interacts with the cell surface in an $\alpha_4\beta_1$ integrin-dependent fashion (Yednock, et al. J. Biol. Chem., 1995, 270:28740).

Recombinant soluble VCAM-1 was expressed as a chimeric fusion protein containing the seven extracellular domains of VCAM-1 on the N-terminus and the human IgG, heavy chain constant region on the C-terminus. The VCAM-1 fusion protein was made and purified by the manner described by Yednock, supra.

Jurkat cells were grown in RPMI 1640 supplemented with 10% fetal bovine serum, penicillin, streptomycin and glutamine as described by Yednock, supra.

Jurkat cells were incubated with 1.5 mM MnCl$_2$ and 5 μg/mL 15/7 antibody for 30 minutes on ice. Mn$^{+2}$ activates the receptor to enhance ligand binding, and 15/7 is a monoclonal antibody that recognizes an activated/ligand occupied conformation of $\alpha_4\beta_1$ integrin and locks the molecule into this conformation thereby stabilizing the VCAM-1/$\alpha_4\beta_1$ integrin interaction. Yednock, et al., supra. Antibodies similar to the 15/7 antibody have been prepared by other investigators (Luque, et al, 1996, J. Biol. Chem. 21:11067) and may be used in this assay.

Cells were then incubated for 30 minutes at room temperature with candidate compounds, in various concentrations ranging from 66 μM to 0.01 μM using a standard 5-point serial dilution. 15 μL soluble recombinant VCAM-1 fusion protein was then added to Jurkat cells and incubated for 30 minutes on ice. (Yednock et al., supra.).

Cells were then washed two times and resuspended in PE-conjugated goat F(ab')$_2$ anti-mouse IgG Fc (Immunotech, Westbrook, Me.) at 1:200 and incubated on ice, in the dark, for 30 minutes. Cells were washed twice and analyzed with a standard fluorescence activated cell sorter ("FACS") analysis as described in Yednock, et al., supra.

Compounds having an IC$_{50}$ of less than about 15 μM possess binding affinity to $\alpha_4\beta_1$.

When tested in this assay, each of the compound prepared in the above examples has or is expected to have an $I_{50}$ of 15 µM or less (or is expected to be active in vivo).

Example B

In vitro Saturation Assay For Determining Binding of Candidate Compounds to $\alpha_4\beta_1$ The following describes an in vitro assay to determine the plasma levels needed for a compound to be active in the Experimental Autoimmune Encephalomyelitis ("EAE") model, described in the next example, or in other in vivo models.

Log-growth Jurkat cells are washed and resuspended in normal animal plasma containing 20 µg/ml of the 15/7 antibody (described in the above example).

The Jurkat cells are diluted two-fold into either normal plasma samples containing known candidate compound amounts in various concentrations ranging from 66 µM to 0.01 µM, using a standard 12 point serial dilution for a standard curve, or into plasma samples obtained from the peripheral blood of candidate compound-treated animals.

Cells are then incubated for 30 minutes at room temperature, washed twice with phosphate-buffered saline ("PBS") containing 2% fetal bovine serum and 1 mM each of calcium chloride and magnesium chloride (assay medium) to remove unbound 15/7 antibody.

The cells are then exposed to phycoerythrin-conjugated goat F(ab')$_2$ anti-mouse IgG Fc (Immunotech, Westbrook, Me.), which has been adsorbed for any non-specific cross-reactivity by co-incubation with 5% serum from the animal species being studied, at 1:200 and incubated in the dark at. 4° C. for 30 minutes.

Cells are washed twice with assay medium and resuspended in the same. They are then analyzed with a standard fluorescence activated cell sorter ("FACS") analysis as described in Yednock et al. J. Biol. Chem., 1995, 270:28740.

The data is then graphed as fluorescence versus dose, e.g., in a normal dose-response fashion. The dose levels that result in the upper plateau of the curve represent the levels needed to obtain efficacy in an in vivo model.

This assay may also be used to determine the plasma levels needed to saturate the binding sites of other integrins, such as the $\alpha_9\beta_1$ integrin, which is the integrin most closely related $\alpha_4\beta_1$ (Palmer et al, 1993, J. Cell Bio., 123:1289). Such binding is predictive of in vivo utility for inflammatory conditions mediated by $\alpha_9\beta_1$ integrin, including by way of example, airway hyper-responsiveness and occlusion that occurs with chronic asthma, smooth muscle cell proliferation in atherosclerosis vascular occlusion following angioplasty, fibrosis and glomerular scarring as a result of renal disease, aortic stenosis, hypertrophy of synovial membranes in rheumatoid arthritis, and inflammation and scarring that occur with the progression of ulcerative colitis and Crohn's disease.

Accordingly, the above-described assay may be performed with a human colon carcinoma cell line, SW 480 (ATTC #CCL228) transfected with cDNA encoding $\alpha_9$ integrin (Yokosaki et al., 1994, J. Biol. Chem., 269:26691), in place of the Jurkat cells, to measure the binding of the $\alpha_9\beta_1$ integrin. As a control, SW 480 cells which express other $\alpha$ and $\beta_1$ subunits may be used.

Accordingly, another aspect of this invention is directed to a method for treating a disease in a mammalian patient, which disease is mediated by $\alpha_9\beta_1$, and which method comprises administering to said patient a therapeutically effective amount of a compound of this invention. Such compounds are preferably administered in a pharmaceutical composition described herein above. Effective daily dosing will depend upon the age, weight, condition of the patient which factors can be readily ascertained by the attending clinician. However, in a preferred embodiment, the compounds are administered from about 20 to 500 µg/kg per day.

Example C

In Vivo Evaluation

The standard multiple sclerosis model, Experimental Autoimmune (or Allergic) Encephalomyelitis ("EAE"), was used to determine the effect of candidate compounds to reduce motor impairment in rats or guinea pigs. Reduction in motor impairment is based on blocking adhesion between leukocytes and the endothelium and correlates with anti-inflammatory activity in the candidate compound. This model has been previously described by Keszthelyi et al., Neurology, 1996, 47:1053-1059, and measures the delay of onset of disease.

Brains and spinal cords of adult Hartley guinea pigs were homogenized in an equal volume of phosphate-buffered saline. An equal volume of Freund's complete adjuvant (100 mg *mycobacterium tuberculosis* plus 10 ml Freund's incomplete adjuvant) was added to the homogenate. The mixture was emulsified by circulating it repeatedly through a 20 ml syringe with a peristaltic pump for about 20 minutes.

Female Lewis rats (2-3 months old, 170-220 g) or Hartley guinea pigs (20 day old, 180-200) were anesthetized with isoflurane and three injections of the emulsion, 0.1 ml each, were made in each flank. Motor impairment onset is seen in approximately 9 days.

Candidate compound treatment began on Day 8, just before onset of symptoms. Compounds were administered subcutaneously ("SC"), orally ("PO") or intraperitoneally ("IP"). Doses were given in a range of 10 mg/kg to 200 mg/kg, bid, for five days, with typical dosing of 10 to 100 mg/kg SC, 10 to 50 mg/kg PO, and 10 to 100 mg/kg IP.

Antibody GG5/3 against $\alpha_4\beta_1$ integrin (Keszthelyi et al., Neurology, 1996, 47:1053-1059), which delays the onset of symptoms, was used as a positive control and was injected subcutaneously at 3 mg/kg on Day 8 and 11.

Body weight and motor impairment were measured daily. Motor impairment was rated with the following clinical score:

| | |
|---|---|
| 0 | no change |
| 1 | tail weakness or paralysis |
| 2 | hindlimb weakness |
| 3 | hindlimb paralysis |
| 4 | moribund or dead |

A candidate compound was considered active if it delayed the onset of symptoms, e.g., produced clinical scores no greater than 2 or slowed body weight loss as compared to the control.

Example D

Asthma Model

Inflammatory conditions mediated by $\alpha_4\beta_1$ integrin include, for example, airway hyper-responsiveness and occlusion that occurs with chronic asthma. The following describes an asthma model which can be used to study the in vivo effects of the compounds of this invention For use in treating asthma.

Following the procedures described by Abraham et al, J. Clin. Invest, 93:776-787 (1994) and Abraham et al, Am J. Respir Crit Care Med, 156:696-703 (1997), both of which are incorporated by reference in their entirety. Compounds of this invention are formulated into an aerosol and administered to sheep which are hypersensitive to *Ascaris suum* antigen. Compounds which decrease the early antigen-induced bronchial response and/or block the late-phase airway response, e.g., have a protective effect against antigen-induced late responses and airway hyper-responsiveness ("AHR"), are considered to be active in this model.

Allergic sheep which are shown to develop both early and late bronchial responses to inhaled *Ascaris suum* antigen are used to study the airway effects of the candidate compounds. Following topical anesthesia of the nasal passages with 2% lidocaine, a balloon catheter is advanced through one nostril into the lower esophagus. The animals are then intubated with a cuffed endotracheal tube through the other nostril with a flexible fiberoptic bronchoscope as a guide.

Pleural pressure is estimated according to Abraham (1994). Aerosols (see formulation below) are generated using a disposable medical nebulizer that provides an aerosol with a mass median aerodynamic diameter of 3.2 μm as determined with an Andersen cascade impactor. The nebulizer is connected to a dosimeter system consisting of a solenoid valve and a source of compressed air (20 psi). The output of the nebulizer is directed into a plastic T-piece, one end of which is connected to the inspiratory port of a piston respirator. The solenoid valve is activated for 1 second at the beginning of the inspiratory cycle of the respirator. Aerosols are delivered at $V_T$ of 500 ml and a rate of 20 breaths/minute. A 0.5% sodium bicarbonate solution only is used as a control.

To assess bronchial responsiveness, cumulative concentration-response curves to carbachol can be generated according to Abraham (1994). Bronchial biopsies can be taken prior to and following the initiation of treatment and 24 hours after antigen challenge. Bronchial biopsies can be preformed according to Abraham (1994).

An in vitro adhesion study of alveolar macrophages can also be performed according to Abraham (1994), and a percentage of adherent cells is calculated.

Aerosol Formulation

A solution of the candidate compound in 0.5% sodium bicarbonate/saline (w/v) at a concentration of 30.0 mg/mL is prepared using the following procedure:

A. Preparation of 0.5% Sodium Bicarbonate/Saline Stock Solution: 100.0 mL

| Ingredient | Gram/100.0 mL | Final Concentration |
|---|---|---|
| Sodium Bicarbonate | 0.5 g | 0.5% |
| Saline | q.s. ad 100.0 mL | q.s ad 100% |

Procedure:

1. Add 0.5 g sodium bicarbonate into a 100 mL volumetric flask.

2. Add approximately 90.0 mL saline and sonicate until dissolved.

3. Q.S. to 100.0 mL with saline and mix thoroughly.

B. Preparation of 30.0 mg/mL Candidate Compound: 10.0 mL

| Ingredient | Gram/10.0 mL | Final Concentration |
|---|---|---|
| Candidate Compound | 0.300 g | 30.0 mg/mL |
| 0.5% Sodium Bicarbonate/Saline Stock Solution | q.s. ad 10.0 mL | q.s ad 100% |

Procedure:

1. Add 0.300 g of the candidate compound into a 10.0 mL volumetric flask.

2. Add approximately 9.7 mL of 0.5% sodium bicarbonate/saline stock solution.

3. Sonicate until the candidate compound is completely dissolved.

4. Q.S. to 10.0 mL with 0.5% sodium bicarbonate/saline stock solution and mix thoroughly.

Using a conventional oral formulation, compounds of this invention would be active in this model.

Example E

Allograft Model

Allograft rejection, associated with infiltration of inflammatory cells, is the leading obstacle to long-term allograft survival. Cell surface adhesion molecules facilitate alloantigen recognition in vitro and may be critical for lymphocyte traffic in vivo. The following describes a model which can be used to study the in vivo effects of the compounds of this invention in the control of allograft rejection.

The following procedures are described in Coito et al., *Transplantation* (1998) 65(6):699-706 and in Korom et al., *Transplantation* (1998) 65(6):854-859, both of which are incorporated by reference in their entirety.

Following the procedures described in Coito and Korom, male adult rats weighing approximately 200-250 g are used in this model. Lewis rats are used as the recipients of cardiac allografts from Lewis X Brown Norway rats. Hearts are transplanted into the abdominal great vessels using standard microvascular techniques.

A candidate compound is administered to the transplant recipient in a suitable pharmaceutical carrier for a 7-day course of treatment starting the day of the engraftment. Doses range from 0.3 to 30 mg/kg/day. Control recipients receive the pharmaceutical carrier only. The rats are euthanized and their cardiac allografts are analyzed as described in Coito and Korom.

Using conventional formulations, compounds of this invention would be active in this model.

What is claimed is:

1. A method for treating a disease in a patient, said disease selected from the group consisting of asthma and multiple sclerosis which method comprises administering to said patient a pharmaceutical composition comprising a pharmaceutically acceptable carrier and a therapeutically effective amount of a compound of formula (Ia) or (Ib):

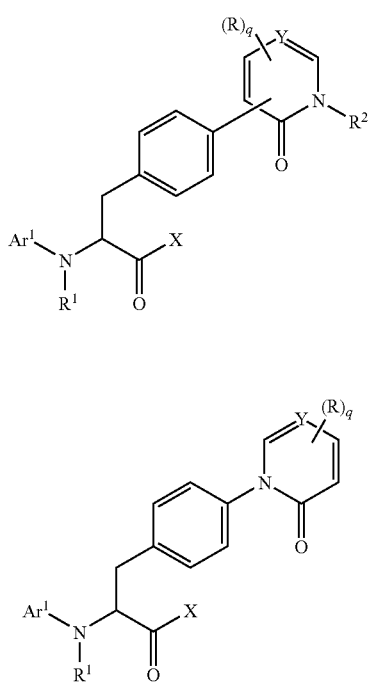

(Ia)

(Ib)

wherein:
Ar[1] is pyrimidinyl optionally substituted with 1-3 substituents selected from the group consisting of alkyl, substituted alkyl, amino, substituted amino, aryl, substituted aryl, cycloalkyl, substituted cycloalkyl, heteroaryl, substituted heteroaryl, heterocyclic and substituted heterocyclic;
R is selected from the group consisting of alkyl, alkoxy, halo, and mono- and dialkyl-amino;
q is an integer from 0 to 2;
R[1] is selected from the group consisting of hydrogen and alkyl;
Y is CH or N;
R[2] is selected from the group consisting of alkyl, substituted alkyl, aryl, substituted aryl, heteroaryl, substituted heteroaryl, cycloalkyl, substituted cycloalkyl, cycloalkenyl, and substituted cycloalkenyl; and
X is selected from the group consisting of hydroxyl, alkoxy and substituted alkoxy;
or an enantiomer, diastereomer or pharmaceutically acceptable salt thereof;
wherein the compound of Formula I(a) or I(b) has a binding affinity to VLA-4 as expressed by an $IC_{50}$ of about 15 μM or less.

2. The method of claim 1 wherein R[1] is hydrogen.
3. The method of claim 2 wherein Y is CH.
4. The method of claim 2 wherein Y is N.
5. The method of claim 3 wherein X is hydroxy.
6. The method of claim 4 wherein X is hydroxy.
7. The method of claim 5 wherein q is zero.
8. The method of claim 5 wherein q is one and R is alkoxy.
9. The method of claim 6 wherein q is zero.
10. The method of claim 6 wherein q is one and R is alkoxy.
11. A method for treating a disease in a patient, said disease selected from the group consisting of inflammatory bowel disease, ulcerative colitis, and Crohn's disease which method comprises administering to said patient a pharmaceutical composition comprising a pharmaceutically acceptable carrier and a therapeutically effective amount of a compound of formula (Ia) or (Ib):

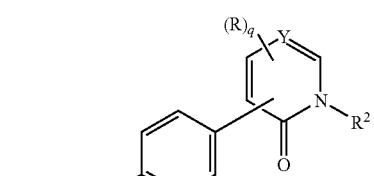

(Ia)

(Ib)

wherein:
Ar[1] is pyrimidinyl optionally substituted with 1-3 substituents selected from the group consisting of alkyl, substituted alkyl, amino, substituted amino, aryl, substituted aryl, cycloalkyl, substituted cycloalkyl, heteroaryl, substituted heteroaryl, heterocyclic and substituted heterocyclic;
R is selected from the group consisting of alkyl, alkoxy, halo, and mono- and dialkyl-amino;
q is an integer from 0 to 2;
R[1] is selected from the group consisting of hydrogen and alkyl;
Y is CH or N;
R[2] is selected from the group consisting of alkyl, substituted alkyl, aryl, substituted aryl, heteroaryl, substituted heteroaryl, cycloalkyl, substituted cycloalkyl, cycloalkenyl, and substituted cycloalkenyl; and
X is selected from the group consisting of hydroxyl, alkoxy and substituted alkoxy;
or an enantiomer, diastereomer or pharmaceutically acceptable salt thereof;
wherein the compound of Formula I(a) or I(b) has a binding affinity to VLA-4 as expressed by an $IC_{50}$ of about 15 μM or less.

12. A method for treating rheumatoid arthritis in a patient which method comprises administering to said patient a pharmaceutical composition comprising a pharmaceutically acceptable carrier and a therapeutically effective amount of a compound of formula (Ia) or (Ib):

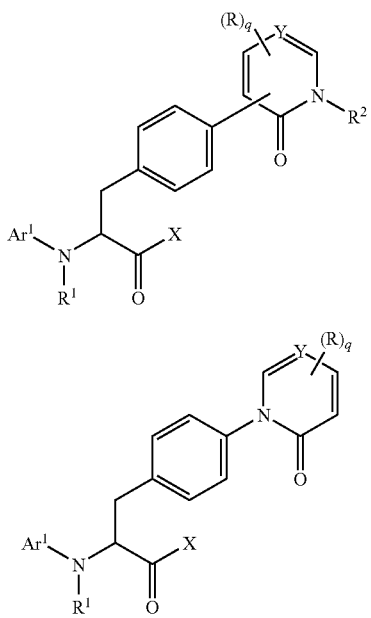

wherein:

Ar$^1$ is pyrimidinyl optionally substituted with 1-3 substituents selected from the group consisting of alkyl, substituted alkyl, amino, substituted amino, aryl, substituted awl, cycloalkyl, substituted cycloalkyl, heteroaryl, substituted heteroaryl, heterocyclic and substituted heterocyclic;

R is selected from the group consisting of alkyl, alkoxy, halo, and mono- and dialkyl-amino;

q is an integer from 0 to 2;

R$^1$ is selected from the group consisting of hydrogen and alkyl;

Y is CH or N;

R$^2$ is selected from the group consisting of alkyl, substituted alkyl, awl, substituted aryl, heteroaryl, substituted heteroaryl, cycloalkyl, substituted cycloalkyl, cycloalkenyl, and substituted cycloalkenyl; and X is selected from the group consisting of hydroxyl, alkoxy and substituted alkoxy;

or an enantiomer, diastereomer or pharmaceutically acceptable salt thereof;

wherein the compound of Formula I(a) or I(b) has a binding affinity to VLA-4 as expressed by an IC$_{50}$ of about 15 µM or less.

* * * * *